(12) United States Patent
Yang

(10) Patent No.: US 9,163,088 B2
(45) Date of Patent: Oct. 20, 2015

(54) TUMOR ANTIGENS ELICIT ANTI-TUMOR HUMORAL IMMUNE REACTIONS IN A SUBSET OF PATIENTS WITH POLYCYTHEMIA VERA

(75) Inventor: Xiao-Feng Yang, Huntingdon Valley, PA (US)

(73) Assignee: Temple University, Philadelphia, PA (US)

( * ) Notice: Subject to any disclaimer, the term of this patent is extended or adjusted under 35 U.S.C. 154(b) by 804 days.

(21) Appl. No.: 12/446,849

(22) PCT Filed: Oct. 26, 2007

(86) PCT No.: PCT/US2007/082605
§ 371 (c)(1),
(2), (4) Date: Apr. 23, 2009

(87) PCT Pub. No.: WO2008/057795
PCT Pub. Date: May 15, 2008

(65) Prior Publication Data
US 2009/0304736 A1  Dec. 10, 2009

Related U.S. Application Data

(60) Provisional application No. 60/863,194, filed on Oct. 27, 2006, provisional application No. 60/868,585, filed on Dec. 5, 2006.

(51) Int. Cl.
*C07K 7/00* (2006.01)
*C07K 16/30* (2006.01)

(52) U.S. Cl.
CPC ..................... *C07K 16/30* (2013.01)

(58) Field of Classification Search
None
See application file for complete search history.

(56) References Cited

FOREIGN PATENT DOCUMENTS

WO    WO2005035724    4/2005
WO    WO2008/021290   *  2/2008  ............... C12Q 1/00

OTHER PUBLICATIONS

International Search Report for PCT/US07/82605 dated Oct. 26, 2007.
Xiong, Z., Novel tumor antigens elecit anti-tumor humoral immune reactions in a subset of patients with polycythemia vera, Clinical Immunology, 2007, 122, pp. 279-287.
Xiong, Z., A novel unconventional antigen MPD5 elicits anti-tumor humoral immune responses in a subset of patients with polycythemia vera, Int J Immunopath Pharm, 2007, 20: 373-380.
Lodish, H, et al., 2004, Molecular Cell Biology, 4th Edition, New York, NY, W.H. Freeman; 2000.
Biochemistry: By D Voet and J G Voet, pp. 126-128, 228-231, John Wiley and Sons, New York 1990.
Mikayama et al, PNAS, 1993, 90:10056-10060.
Protein Expression and Purification Core Facility Cloning: Choice of Expression Systems, www.embl.de/pepcore/pepcore services/cloning/choice expression systems/ retrieved Aug. 18, 2014.

* cited by examiner

*Primary Examiner* — Mark Halvorson
(74) *Attorney, Agent, or Firm* — Caesar Rivise, PC

(57) ABSTRACT

The invention provides novel antigens, MPD5, PV13, and PV65, which belongs to the group of cryptic antigens without conventional genomic structure and is encoded by a cryptic open reading frame located in the 3'untranslated region (3'UTR) of myotrophin mRNA. The antigens elicit IgG antibody responses in a subset of PV patients, as well as patients with chronic myelogenous leukemia and prostate cancer. The translation of MPD5, PV13 and PV65 was mediated by a novel internal ribosome entry site (IRES) upstream of the open reading frame. Eliciting anti-tumor immune response against MPD5, PV13 and/or PV65 antigen in patients with myeloproliferative diseases is a novel immunotherapy.

8 Claims, 11 Drawing Sheets

MPD5 protein (47 a.a.)
MPD5 Peptide (a.a.30-47)
MGSNPDSAICGFMTLPKLLNLPLCKIRKTTLNLSTGQASSPQCLLPS

N1 N2 N3 N4 N5 N6 N7 N8 N9 N10 eIF2α — 2.1 kb
β-Actin — 1.8 kb

T1 T2 T3 T4 T5 T6 T7 T8 T9 T10 eIF2α — 2.1 kb
β-Actin — 1.8 kb ly donors, suggesting that they are authentic tumor antigens, suggesting that they are immunogenic tumor antigens. Increased phosphorylation of PV65 in response to stimulation of IFN-α, and upregulation of PV13 in tumor cells might enhance their abilities in elicitation of immune reactions in patients. These findings provide new insights into the mechanism underlying the regulation of the self-antigen repertoire in eliciting anti-tumor immune reactions in patients with polycythemia vera, and suggest their potential as the targets of novel immunotherapy. This invention is the first demonstration that phosphorylation of tumor antigen increases the immunogenicity of tumor antigens, suggesting posttranslational modifications of proteins, such as phosphorylation, can be targeted for diagnosis and immunotherapy. These antigens can elicit anti-tumor IgG antibody responses, and T cell responses. Since these two tumor antigens are non-mutated antigens, therefore, this antigen can be used for diagnosis, prognosis and immunotherapy for viral infections, inflammation, autoimmune diseases and tumors. The inventor has discovered that polycythemia vera is a myeloproliferative disease. This invention is the first report showing that anti-tumor immune responses, elicited by these self-tumor antigens, MPD5, PV13 (protamine 2) and PV65 (eIF-2α), leads to tumor remission. The inventor has found that immune responses to MPD5, PV13 and PV65 self-tumor antigens can be targeted for the purposes of diagnosis, prognosis and immunotherapy for viral infections, inflammation, autoimmune diseases and tumors. The inventor has further found that interferon-α stimulation enhances anti-tumor immune responses via promotion of posttranslational modifications of protein antigens.

SEQUENCE LISTING

```
<160> NUMBER OF SEQ ID NOS: 19

<210> SEQ ID NO 1
<211> LENGTH: 1517
<212> TYPE: DNA
<213> ORGANISM: Homo sapiens

<400> SEQUENCE: 1
cagccctgca ggaacctagc ctgtcttaac ctacttggct ttgcagcatg caacaggagc      60
aaagcacgac aaaggcagcc agatgtggtt taaggtgagg aactctggaa tcagagacat     120
gggttcgaat cccgactctg ccatttgtgg gtttatgacc ctgcccaagt tacttaacct     180
ccctctctgt aagatcagga aaacgacact gaacctcagc acaggccagg catccagccc     240
acagtgcctg ctaccttcct agtacagtgg ggagaccatg ggctctgctc agacaagcct     300
gggttcaaat ccagctctgc tgcgtattag cacatggtct ttggcgcatt ctctcatctc     360
```

```
tctgtgcccc agtttcctca tctgtaaatg ggcatcgtga cagcttccat cttagtgttg      420
gtgagtggac tgggtaaaat acagcaccag acctagcaca cagtatatcc tcagtaaatg      480
gggacatggc cgggcatggt ggctcatgcc tgtaattcca gcactttggg aggccaaggc      540
gggcggatca cctgaggtca ggagttcgag accagcctgg ctggccaaca cagtgaaacc      600
ccatctctac taaaaataca aaattatctg ggcgtggtg gcacctgcct ataatcccag       660
ctactcagga ggaggctgag gcaggaggct cacttgaacc caggaggcag agggtgcagg      720
gagctgagat tgcgccactg tactccagcc tgggattcac acttggagcc taggagaggt      780
ataaataaat caaaagatcc gtctacttag cagggcaggc agagaggccc ccacatacac      840
aggcaagtct agggtcagcc ccccaggcct ggctggagag agacaagaac aaagacagga      900
gagcctggag gatatttagg aaaacacacg tcctcgggtg cccggccgag ggcccacca       960 cagcctccgc tcgcccagcc tgtgtatgca gagagggtcc tgccagtggc cctgccgcag     1020
cctggctcta agacctttgc ctctgtcagg cccagccagg ctctgagtct gccctcctgg     1080
cccctggttc accggatcag gcccagcccc gaccccagc catgccagg ccgcttctct       1140 ctccacgggc tccctggctc gggggccatc actgtgcaaa ggcctggtgg gcgcaaaggg     1200
ggccggcccc tcaacctcag taataaacac gctcgcacgg ccctgcacac tcgttatact     1260
cacacccaca caggcatact ttcgcccttc taggctcacg catgtgcttg cacacaaatc     1320
actttggaat gcacacacgt gcacacacac actccctgag acccgcacgt actccctgcg     1380
gcgcccggca cactcctccg cccgtcgtcc ccactcggga agtgggtagc ggggagccat     1440
gcccgcgtcc ccgcacgcac tcaccccaac aacgccacca gacgctccgg ggtgcacacg     1500
cacacccgcc ggggacc                                                    1517
```

<210> SEQ ID NO 2
<211> LENGTH: 47
<212> TYPE: PRT
<213> ORGANISM: Homo sapiens

<400> SEQUENCE: 2

Met Gly Ser Asn Pro Asp Ser Ala Ile Cys Gly Phe Met Thr Leu Pro
1               5                   10                  15

Lys Leu Leu Asn Leu Pro Leu Cys Lys Ile Arg Lys Thr Thr Leu Asn
            20                  25                  30

Leu Ser Thr Gly Gln Ala Ser Ser Pro Gln Cys Leu Leu Pro Ser
        35                  40                  45

<210> SEQ ID NO 3
<211> LENGTH: 3894
<212> TYPE: DNA
<213> ORGANISM: Homo sapiens

<400> SEQUENCE: 3

```
ctctttccgg gacaacatgg cgccgtccac gccgctcttg acagtccgag gatcagaagg       60
actgtacatg gtgaatggac caccacattt tacagaaagc acagtgtttc caagggaatc      120
tgggaagaat tgcaaagtct gtatctttag taaggatggg accttgtttg cctggggcaa      180
tggagaaaaa gtaatatta tcagtgtcac taacaaggga ctactgcact ccttcgacct       240
cctgaaggca gtttgccttg aattctcacc caaaaatact gtcctggcaa cgtggcagcc      300
ttacactact tctaaagatg gcacagctgg gataccaaac ctacaacttt atgatgtgaa      360
aactgggaca tgtttgaaat ctttcatcca gaaaaaaatg caaaattggt gtccatcctg      420
```

-continued

```
gtcagaagat gaaactcttt gtgcccgcaa tgttaacaat gaagttcact tcttttgaaaa    480
caacaatttt aacacaattg caaataaatt gcatttgcaa aaaattaatg attttgtatt    540
atcacctgga ccccaaccat acaaggtggc tgtctatgtt ccaggaagta aaggtgcacc    600
ttcatttgtt agattatatc agtacccaa ctttgctgga cctcatgcag ctttagctaa    660
taaaagtttc tttaaggcag ataaagttac aatgctgtgg aataaaaaag ctactgctgt    720
gttggtaata gctagcacag atgttgacaa gacaggagct tcctactatg agaacaaac    780
tctacactac attgcaacaa atggagaaag tgctgtagtg caattaccaa aaaatggccc    840
catttatgat gtagtttgga attctagttc tactgagttt tgtgctgtat atggttttat    900
gcctgccaaa gcgacaattt tcaacttgaa atgtgatcct gtatttgact ttggaactgg    960
tcctcgtaat gcagcctact atagccctca tggacatata ttagtattag ctggatttgg   1020
aaatctgagg ggacaaatgg aagtgtggga tgtgaaaaac tacaaactta tttctaaacc   1080
ggtggcttct gattctacat attttgcttg gtgcccggat ggtgagcata ttttaacagc   1140
tacatgtgct cccaggttac gggttaataa tggatacaaa atttggcatt atactggctc   1200
tatcttgcac aagtatgatg tgccatcaaa tgcagaatta tggcaggttt cttggcagcc   1260
attttttggat ggaatatttc cagcaaaaac aataacttac caagcagttc caagtgaagt   1320
acccaatgag gaacctaaag ttgcaacagc ttatagaccc ccagctttaa gaaataaacc   1380
aatcaccaat tccaaattgc atgaagagga accacctcag aatatgaaac acaatcagg   1440
aaacgataag ccattatcaa aaacagctct taaaaatcaa aggaagcatg aagctaagaa   1500
agctgcaaag caggaagcaa gaagtgacaa gagtccagat ttggcaccta ctcctgcccc   1560
acagagcaca ccacgaaaca ctgtctctca gtcaatttct ggggaccctg agatagacaa   1620
aaaaatcaag aacctaaaga agaaactgaa agcaatcgaa caactgaaag aacaagcagc   1680
aactggaaaa cagctagaaa aaatcagtt ggagaaaatt cagaaagaaa cagcccttct   1740
ccaggagctg gaagatttgg aattgggtat ttaaagattc acggaaagca agttgatgac   1800
cagaaatcag tgcaaacaca tcttctgtta aacccattgg tatacacaga atattcctgt   1860
gcccacactt aatgtcaatc tataatttta accatttatc caagattcta ctaagtgtaa   1920
aattatttaa taatgtctat taaattgata tttatatctt gcatcctata tcatgtcaat   1980
atgtgatata gaaagagat acgtgaattt tttagctaag cttgacagat tgaaagacaa   2040
gtgtcattt tttttgtaga gggtgatata taccatgtaa atgaataaag acattttaaa   2100
tttaatcact gttttattta taagttcctt agttcagata tcctttatta atttataaga   2160
tgtgtaaaac tacttaattc tcacaagact ctatgaagta attcttttaa tctctatttt   2220
ataaatgaaa aaactaaggc cataaattta agaaatttgt cagtgtctca aagctaggaa   2280
atggccatct aatcccagag cctatgcttt aggtcactat gatatatact actcctgtat   2340
cctcaagtaa tgtatcattt agtaacacta agcaccctgc ttagttttca tggatactgc   2400
caaattgccc tatctcaagc tttatacttg caccatttaa agttttccac actgttggca   2460
atatcagaag tgataaggct ttgaaatgtt cgccactttg ataaagagga aatgattgtt   2520
tgttactgtt atatacatgt attttttatca gagatgggtt atgtacttt ccacgtttga   2580
tagttggttg tatttcttta gtgaattgat ttttcttttc ctttgcccat ttttctgttt   2640
ggatgtttga ctttcttctt aatttgtaag agtatcctat gtagtaacaa atccttttt   2700
taaaatttt taaagaaaaa gtatacacac aggacttttt ttttctaat tcaaaaata   2760
caaaggcatg caatgaaaat taagtctgtt ccactaccac atttccagt tttttgtgta   2820
```

```
-continued tctttctaat gatagatacc atatgagtat tcaaatatac atacacatac acttaaaaaa    2880
aaaagatggc atatactaac tgttctgttt ggggcttttt ggtggtggtg tttgtttgac    2940
agggtctcac tctgcctccc aggttggagt gcaccttgaa ctcctggact caagtgatcc    3000
ttcacctcct ccttccaagt atctgacact acaggcttgc atcactatgc ccagcttata    3060
ctcaccatag tggttctgta ctcccttaaa atattctgga ggccaggcat gctggctcac    3120
acctgtaatc ccagcacctt gggaggccaa ggtgggtgga tcacctgagg tcaggagttc    3180
aagaccagcc tgatcaacat ggtgaaaccc catctctact aaaaatacaa aagtatccag    3240
gcgtggtagc atacctgt aatcccagct acttgggagg ctgaggtagg aaaattgttt     3300
gaacccggca gacagaggtt gcagtgagcc gacatcgtgc cattgcactc caagcctggg    3360
caacaagagt gaaaccgtct cacacacaca caaaaaaaaa tattttggag ctccttctat    3420
atgagtctct ctctcttatc tctctcagga tgtgtgtatg tgtttgtttc tctggaaaac    3480
cctgactaat acagattagc tatgtattag gtaatacata atgcctaata cataactaat    3540
atatggacag gaagttaata gactgactgt gccaccttaa aactcgtatg ttgaagccct    3600
aacctccaac gtggtggtat tgggagatgg gccttttgga aggtaagtgt gtttgaatga    3660
ggtgaagagg ttggggactt cgtgatggga ttattgtcct tacaagaaaa gacaccagag    3720
agcttgttct gtctctttgg gccatgtgaa gacatggtga gaaagcagcc agctgtaagc    3780
cagagagtcc tcaccagaac ctaaccatgc tggtgatatc ctcatctcag acttctaacc    3840
tccagaactg tgagaaaata aacttctttg tttaaaccaa aaaaaaaaaa aaaa          3894

<210> SEQ ID NO 4
<211> LENGTH: 585
<212> TYPE: PRT
<213> ORGANISM: Homo sapiens

<400> SEQUENCE: 4

Met Ala Pro Ser Thr Pro Leu Leu Thr Val Arg Gly Ser Glu Gly Leu
1               5                   10                  15

Tyr Met Val Asn Gly Pro Pro His Phe Thr Glu Ser Thr Val Phe Pro
                20                  25                  30

Arg Glu Ser Gly Lys Asn Cys Lys Val Cys Ile Phe Ser Lys Asp Gly
            35                  40                  45

Thr Leu Phe Ala Trp Gly Asn Gly Glu Lys Val Asn Ile Ile Ser Val
        50                  55                  60

Thr Asn Lys Gly Leu Leu His Ser Phe Asp Leu Leu Lys Ala Val Cys
65                  70                  75                  80

Leu Glu Phe Ser Pro Lys Asn Thr Val Leu Ala Thr Trp Gln Pro Tyr
                85                  90                  95

Thr Thr Ser Lys Asp Gly Thr Ala Gly Ile Pro Asn Leu Gln Leu Tyr
                100                 105                 110

Asp Val Lys Thr Gly Thr Cys Leu Lys Ser Phe Ile Gln Lys Lys Met
            115                 120                 125

Gln Asn Trp Cys Pro Ser Trp Ser Glu Asp Glu Thr Leu Cys Ala Arg
        130                 135                 140

Asn Val Asn Asn Glu Val His Phe Phe Glu Asn Asn Phe Asn Thr
145                 150                 155                 160

Ile Ala Asn Lys Leu His Leu Gln Lys Ile Asn Asp Phe Val Leu Ser
                165                 170                 175

Pro Gly Pro Gln Pro Tyr Lys Val Ala Val Tyr Val Pro Gly Ser Lys
```

```
            180                 185                 190
Gly Ala Pro Ser Phe Val Arg Leu Tyr Gln Tyr Pro Asn Phe Ala Gly
            195                 200                 205

Pro His Ala Ala Leu Ala Asn Lys Ser Phe Phe Lys Ala Asp Lys Val
            210                 215                 220

Thr Met Leu Trp Asn Lys Lys Ala Thr Ala Val Leu Val Ile Ala Ser
225                 230                 235                 240

Thr Asp Val Asp Lys Thr Gly Ala Ser Tyr Tyr Gly Glu Gln Thr Leu
                245                 250                 255

His Tyr Ile Ala Thr Asn Gly Glu Ser Ala Val Val Gln Leu Pro Lys
            260                 265                 270

Asn Gly Pro Ile Tyr Asp Val Val Trp Asn Ser Ser Thr Glu Phe
        275                 280                 285

Cys Ala Val Tyr Gly Phe Met Pro Ala Lys Ala Thr Ile Phe Asn Leu
        290                 295                 300

Lys Cys Asp Pro Val Phe Asp Phe Gly Thr Gly Pro Arg Asn Ala Ala
305                 310                 315                 320

Tyr Tyr Ser Pro His Gly His Ile Leu Val Leu Ala Gly Phe Gly Asn
                325                 330                 335

Leu Arg Gly Gln Met Glu Val Trp Asp Val Lys Asn Tyr Lys Leu Ile
            340                 345                 350

Ser Lys Pro Val Ala Ser Asp Ser Thr Tyr Phe Ala Trp Cys Pro Asp
        355                 360                 365

Gly Glu His Ile Leu Thr Ala Thr Cys Ala Pro Arg Leu Arg Val Asn
        370                 375                 380

Asn Gly Tyr Lys Ile Trp His Tyr Thr Gly Ser Ile Leu His Lys Tyr
385                 390                 395                 400

Asp Val Pro Ser Asn Ala Glu Leu Trp Gln Val Ser Trp Gln Pro Phe
                405                 410                 415

Leu Asp Gly Ile Phe Pro Ala Lys Thr Ile Thr Tyr Gln Ala Val Pro
            420                 425                 430

Ser Glu Val Pro Asn Glu Glu Pro Lys Val Ala Thr Ala Tyr Arg Pro
            435                 440                 445

Pro Ala Leu Arg Asn Lys Pro Ile Thr Asn Ser Lys Leu His Glu Glu
        450                 455                 460

Glu Pro Pro Gln Asn Met Lys Pro Gln Ser Gly Asn Asp Lys Pro Leu
465                 470                 475                 480

Ser Lys Thr Ala Leu Lys Asn Gln Arg Lys His Glu Ala Lys Lys Ala
                485                 490                 495

Ala Lys Gln Glu Ala Arg Ser Asp Lys Ser Pro Asp Leu Ala Pro Thr
            500                 505                 510

Pro Ala Pro Gln Ser Thr Pro Arg Asn Thr Val Ser Gln Ser Ile Ser
            515                 520                 525

Gly Asp Pro Glu Ile Asp Lys Lys Ile Lys Asn Leu Lys Lys Lys Leu
        530                 535                 540

Lys Ala Ile Glu Gln Leu Lys Glu Gln Ala Ala Thr Gly Lys Gln Leu
545                 550                 555                 560

Glu Lys Asn Gln Leu Glu Lys Ile Gln Lys Glu Thr Ala Leu Leu Gln
                565                 570                 575

Glu Leu Glu Asp Leu Glu Leu Gly Ile
            580                 585

<210> SEQ ID NO 5
```

```
<211> LENGTH: 683
<212> TYPE: DNA
<213> ORGANISM: Homo sapiens

<400> SEQUENCE: 5
agaccagacc aacagtaaca ccaagggcag gtgggcaggc ctccgccctc ctcccctact      60
ccagggccca ctgcagcctc agcccaggag ccaccagatc tcccaacacc atggtccgat     120
accgcgtgag gagcctgagc gaacgctcgc acgaggtgta caggcagcag ttgcatgggc     180
aagagcaagg acaccacggc caagaggagc aagggctgag cccggagcac gtcgaggtct     240
acgagaggac ccatggccag tctcactata ggcgcagaca ctgctctcga aggaggctgc     300
accggatcca caggcggcag catcgctcct gcagaaggcg caaaagacgc tcctgcaggc     360
accggaggag gcatcgcaga ggctgcagaa ccaggaagag aacatgcaga aggcactaag     420
cttcctgggc ccctcacccc cagctggaaa ttaagaaaaa gtcgcccgaa acaccaagtg     480
aggccatagc aattccccta catcaaatgc tcaagccccc agctggaagt taagagaaag     540
tcacctgccc aagaaacacc gagtgaggcc atagcaactc ccctacatca aatgctcaag     600
ccctgagttg ccgccagaa gcccacaaga tctgagtgaa acgagcaaaa gtcacctgcc     660
caataaagct tgacaagaca ctc                                            683
```

```
<210> SEQ ID NO 6
<211> LENGTH: 102
<212> TYPE: PRT
<213> ORGANISM: Homo sapiens

<400> SEQUENCE: 6

Met Val Arg Tyr Arg Val Arg Ser Leu Ser Glu Arg Ser His Glu Val
1               5                   10                  15

Tyr Arg Gln Gln Leu His Gly Gln Glu Gln Gly His His Gly Gln Glu
                20                  25                  30

Glu Gln Gly Leu Ser Pro Glu His Val Glu Val Tyr Glu Arg Thr His
        35                  40                  45

Gly Gln Ser His Tyr Arg Arg His Cys Ser Arg Arg Arg Leu His
    50                  55                  60

Arg Ile His Arg Arg Gln His Arg Ser Cys Arg Arg Lys Arg Arg
65                  70                  75                  80

Ser Cys Arg His Arg Arg His Arg Arg Gly Cys Arg Thr Arg Lys
                85                  90                  95

Arg Thr Cys Arg Arg His
            100
```

```
<210> SEQ ID NO 7
<211> LENGTH: 17
<212> TYPE: DNA
<213> ORGANISM: Homo sapiens

<400> SEQUENCE: 7
gaaaagctcg aaagctc                                                    17
```

```
<210> SEQ ID NO 8
<211> LENGTH: 24
<212> TYPE: DNA
<213> ORGANISM: Homo sapiens

<400> SEQUENCE: 8
aacagcagcc ctttctctcc agta                                            24
```

```
<210> SEQ ID NO 9
<211> LENGTH: 23
<212> TYPE: DNA
<213> ORGANISM: Homo sapiens

<400> SEQUENCE: 9
taatacgcag cagagctgga ttg                                              23

<210> SEQ ID NO 10
<211> LENGTH: 32
<212> TYPE: DNA
<213> ORGANISM: Homo sapiens

<400> SEQUENCE: 10
atctggcacc acaccttcta caatgagctg cg                                    32

<210> SEQ ID NO 11
<211> LENGTH: 32
<212> TYPE: DNA
<213> ORGANISM: Homo sapiens

<400> SEQUENCE: 11
cgtcatactc ctgcttgctg atccacatct gc                                    32

<210> SEQ ID NO 12
<211> LENGTH: 20
<212> TYPE: DNA
<213> ORGANISM: Homo sapiens

<400> SEQUENCE: 12
gagaggcagc gaattcatct                                                  20

<210> SEQ ID NO 13
<211> LENGTH: 18
<212> TYPE: DNA
<213> ORGANISM: Homo sapiens

<400> SEQUENCE: 13 aaggggggacc ctgtcctg                                                   18

<210> SEQ ID NO 14
<211> LENGTH: 20
<212> TYPE: DNA
<213> ORGANISM: Homo sapiens

<400> SEQUENCE: 14
gctgagattg cgccactgta                                                  20

<210> SEQ ID NO 15
<211> LENGTH: 21
<212> TYPE: DNA
<213> ORGANISM: Homo sapiens

<400> SEQUENCE: 15
cctctcctag gctccaagtg t                                                21

<210> SEQ ID NO 16
<211> LENGTH: 15
<212> TYPE: DNA
<213> ORGANISM: Homo sapiens

<400> SEQUENCE: 16
tccagcctgg gattc                                                       15
```

```
<210> SEQ ID NO 17
<211> LENGTH: 18
<212> TYPE: PRT
<213> ORGANISM: Homo sapiens

<400> SEQUENCE: 17

Thr Leu Asn Leu Ser Thr Gly Gln Ala Ser Ser Pro Gln Cys Leu Leu
1               5                   10                  15

Pro Ser

<210> SEQ ID NO 18
<211> LENGTH: 144
<212> TYPE: DNA
<213> ORGANISM: Homo sapiens

<400> SEQUENCE: 18
atgggttcga atcccgactc tgccatttgt gggtttatga ccctgcccaa gttacttaac      60
ctccctctct gtaagatcag gaaaacgaca ctgaacctca gcacaggcca ggcatccagc     120
ccacagtgcc tgctaccttc ctag                                            144

<210> SEQ ID NO 19
<211> LENGTH: 54
<212> TYPE: DNA
<213> ORGANISM: Homo sapiens

<400> SEQUENCE: 19
ctgaacctca gcacaggcca ggcatccagc ccacagtgcc tgctaccttc ctag            54
```

TUMOR ANTIGENS ELICIT ANTI-TUMOR HUMORAL IMMUNE REACTIONS IN A SUBSET OF PATIENTS WITH POLYCYTHEMIA VERA

CROSS-REFERENCE TO RELATED APPLICATIONS

This application claims benefit of U.S. Provisional Patent Application No. 60/863,194 filed Oct. 27, 2006, and U.S. Provisional Patent Application No. 60/868,585 filed Dec. 5, 2006, the entire disclosures of which are hereby incorporated by reference in their entireties.

STATEMENT REGARDING FEDERALLY SPONSORED RESEARCH OR DEVELOPMENT

This research was supported in part by U.S. Government funds (NIH Grant No. AI054514), and the U.S. Government may therefore have certain rights in the invention.

BACKGROUND OF THE INVENTION

1. Field of Invention

This invention relates to self-tumor antigens and methods and compositions to generate immunity in humans against self tumor antigens. This invention is more particularly related to eliciting or enhancing immunity against human self tumor antigen encoded by unconventional reading frames with homology to foreign proteins 2. Description of Related Art Self-tumor antigens that elicit anti-tumor immune responses in responses to interferon-α (IFN-α) stimulation remain poorly defined. Currently, most of tumor antigens and autoantigens are encoded by primary open reading frames in mRNAs.

A new generation of tumor antigens has been defined as "self proteins" (J. Exp. Med. 180:1-4, 1994; Cell 82:13-17, 1995). Self tumor antigens are proteins that are expressed by both normal cells and cancer cells. (As opposed to mutated proteins that are unique and thus cancer specific.) Self tumor antigens are typically overexpressed by the cancer cells. Certain self proteins, such as HER-2/neu and c-myc, are known to be involved in malignant transformation. See U.S. Patent Publication No. 2002/0019331 to Cheever.

Internal ribosome entry site associated studies have been extensive in biochemistry field but not immunology fields, e.g., tumor immunology field. The practical use of internal ribosome entry site is limited in construction of bicistronic vectors for gene therapy and construction of bicistronic vectors for gene expression.

Due to the difficulties in the current approaches to treatment and prevention of cancer, there is a need in the art for improved methods and compositions. The present invention fulfills this need, and further provides other related advantages.

The invention provides several new self-tumor antigens, MPD5, PV65 (eIF-2α) and PV13 (protamine 2), which have been found to be immunogenic in patients with polycythemia vera, a myeloproliferative disease. These conventional self-tumor antigens can be used for diagnosis and prognosis, as well as the target for future immunotherapy.

The inventor screened a human testis cDNA library with sera from three polycythemia vera (PV) patients who responded to IFN-α and identified novel antigens, MPD5, PV13 (protamine 2) and PV65 (eIF-2α). These antigens elicit IgG antibody responses in a subset of PV patients but not in All references cited herein are incorporated herein by reference in their entireties.

BRIEF SUMMARY OF THE INVENTION

The invention provides an isolated nucleic acid sequence selected from the group consisting of SEQ ID NO: 1, SEQ ID NO: 3, SEQ ID NO: 5, SEQ ID NO: 18, SEQ ID NO: 19, fragments thereof, variants thereof, and muteins thereof.

The invention provides an isolated nucleic acid sequence encoding a polypeptide selected from the group consisting of SEQ ID NO: 2, SEQ ID NO: 4, SEQ ID NO: 6, SEQ ID NO: 17, fragments thereof, muteins thereof, and variants thereof.

The invention provides a nucleic acid comprising a reporter gene operatively linked to an IRES region selected from the group consisting of an MPD5-IRES region, a PV65-IRES region, a PV13-IRES region, wherein the IRES region is responsive to IFN-α. The invention further provides the nucleic acid, further comprising a nucleic acid sequence selected from the group consisting of SEQ ID NO: 1, SEQ ID NO: 3, SEQ ID NO: 5, SEQ ID NO: 18, SEQ ID NO: 19, fragments thereof, variants thereof, and muteins thereof. The invention further provides the nucleic acid, wherein the reporter gene is a luciferase gene. The invention further provides the nucleic acid, further comprising a nucleic acid sequence encoding a polypeptide selected from the group consisting of SEQ ID NO: 2, SEQ ID NO: 4, SEQ ID NO: 6, SEQ ID NO: 17, fragments thereof, muteins thereof, and variants thereof, wherein the IRES region is responsive to IFN-α.

The invention provides a bicistronic reporter vector comprising a first reporter gene, an IRES region selected from the group consisting of an MPD5-IRES region, a PV65-IRES region, a PV13-IRES region, and a second reporter gene, wherein the IRES region is responsive to IFN-α.

The invention provides a host cell comprising a nucleic acid, wherein the IRES region is responsive to IFN-α. The invention provides a host cell, wherein the host cell is a member selected from the group consisting of eukaryotic cells and prokaryotic cells.

The invention provides a cell line stably transfected with the nucleic acid, wherein the IRES region is responsive to IFN-α.

The invention provides a substantially purified polypeptide selected from the group consisting of SEQ ID NO: 2, SEQ ID NO: 4, SEQ ID NO: 6, SEQ ID NO: 17, fragments thereof, muteins thereof, and variants thereof.

The invention provides a vaccine for the protection of humans against cancer, comprising: a recombinant vector virus that expresses in vivo a heterologous nucleic acid sequence selected from the group consisting of: SEQ ID NO: 1, SEQ ID NO: 3, SEQ ID NO: 5, SEQ ID NO: 18, SEQ ID NO: 19, a nucleic acid sequence encoding SEQ ID NO: 2, SEQ ID NO: 4, SEQ ID NO: 6, SEQ ID NO: 17, fragments thereof, muteins thereof, and variants thereof, together with a pharmaceutically acceptable carrier.

The invention provides a vaccine composition comprising an immunogenic peptide selected from the group consisting of SEQ ID NO: 2, SEQ ID NO: 4, SEQ ID NO: 6, SEQ ID NO: 17, fragments thereof, muteins thereof, and variants thereof.

The invention provides an immunogenic peptide selected from the group consisting of SEQ ID NO: 2, SEQ ID NO: 4, SEQ ID NO: 6, SEQ ID NO: 17, fragments thereof, muteins thereof, and variants thereof.

The invention provides an isolated nucleic acid encoding an immunogenic peptide selected from the group consisting of SEQ ID NO: 2, SEQ ID NO: 4, SEQ ID NO: 6, SEQ ID NO: 17, fragments thereof, muteins thereof, and variants thereof.

The invention provides an isolated antibody, wherein said antibody selectively binds: a) a peptide selected from the group consisting of an MPD5 peptide, a PV65 peptide, a PV13 peptide, SEQ ID NO: 2, SEQ ID NO: 4, SEQ ID NO: 6, SEQ ID NO: 17, fragments thereof, muteins thereof, and variants thereof; b) a peptide selected from the group consisting of an MPD5 peptide, a PV65 peptide, a PV13 peptide that is encoded by a nucleic acid molecule that hybridizes to the nucleic acid sequence of SEQ ID NO: 1, SEQ ID NO; 3, or SEQ ID NO: 5, SEQ ID NO: 18, SEQ ID NO: 19, under stringent conditions, comprising 50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; c) a fragment of said antibody, wherein said antibody and antibody fragment selectively bind to said polypeptide. The invention further provides an antibody which is of polyclonal or monoclonal origin.

The invention provides a method of eliciting or enhancing an immune response to a human self tumor antigen, comprising immunizing a human being an antigen selected from the group consisting of an MPD5 antigen, a PV65 antigen, and a PV13 antigen, wherein the antigen is homologous to foreign proteins or foreign peptides but normally not expressed unless stimulated by interferons or cytokines.

The invention provides a method of treating or preventing a disorder selected from the group consisting of viral infections, inflammation, autoimmune disease, polycythemia vera, and cancer comprising administering to said subject a therapeutically effective amount of a vaccine composition according to the invention.

The invention provides a method of identifying a potential therapeutic agent for the treatment of a disorder selected from the group consisting of viral infections, inflammation, autoimmune disease, polycythemia vera, and cancer which inhibits IFN-α induced expression of an MPD5 peptide, a PV65 peptide, and/or a PV13 peptide comprising the steps of: (a) providing a reporter vector comprising a reporter gene and an IRES region selected from the group consisting of an MPD5-IRES region, a PV65-IRES region, a PV13-IRES region, wherein the region is responsive to IFN-α; (b) providing a test agent; (c) providing IFN-α; (d) combining the reporter vector, the test agent, and IFN-α; (e) measuring reporter gene activity in the presence of test agent; (f) measuring reporter gene activity in a control sample; and (g) comparing reporter gene activity in the control sample compared to the test sample, to identify a compound which modulates a disorder selected from the group consisting of viral infections, inflammation, autoimmune disease, and cancer. The invention further provides that the reporter vector comprising a reporter gene and an IRES region selected from the group consisting of an MPD5-IRES region, a PV65-IRES region, a PV13-IRES region, wherein the IRES region is responsive to IFN-α is in a stably transfected cell line. The invention further provides that the cell is a member selected from the group consisting of eukaryotic cells, and prokaryotic cells. The invention further provides that the reporter gene is a luciferase gene.

The invention provides a method of treating a disorder selected from the group consisting of viral infections, inflammation, autoimmune disease, polycythemia vera, and cancer in a patient in need thereof by administration of an effective amount of a compound which modulates the activity of a member of the group selected from an MPD5 peptide, a PV65 peptide, a PV13 peptide, an MPD5-IRES region, a PV65-IRES region, and/or a PV13-IRES region activity, and combinations thereof.

The invention provides a kit comprising an immunogenic peptide comprising an immunogenic peptide selected from the group consisting of SEQ ID NO: 2, SEQ ID NO: 4, SEQ ID NO: 6, SEQ ID NO: 17, fragments thereof, muteins thereof, and variants thereof The invention provides a method of identifying a potential therapeutic agent which inhibits a disorder selected from the group consisting of viral infections, inflammation, autoimmune disease, and cancer comprising the steps of: (a) providing a cell comprising a reporter gene operatively linked to an IRES region selected from the group consisting of an MPD5-IRES region, a PV65-IRES region, a PV13-IRES region, wherein the IRES region is responsive to IFN-α; (b) contacting the cell with a test agent in the presence of IFN-α, wherein a decrement in the expression of the reporter gene in the presence of IFN-α and the test agent, as compared to the expression of the reporter gene in the presence of IFN-α and the absence of the test agent, indicates that the test agent is a potential cancer therapeutic.

The invention provides a method of identifying a potential therapeutic agent which a disorder selected from the group consisting of viral infections, inflammation, autoimmune disease, and cancer comprising the steps of: (a) providing a cell comprising a reporter gene operatively linked to an MPD5-IRES region, and the reporter gene; (b) contacting said cell with a test agent under conditions wherein said cells express the reporter gene, wherein a decrement in the expression of the reporter gene as compared to a control indicates that the test agent is a potential therapeutic for a disorder selected from the group consisting of viral infections, inflammation, autoimmune disease, and cancer. The invention further provides that the cell is a member selected from the group consisting of eukaryotic cells, and prokaryotic cells. The invention further provides that the reporter gene is a luciferase gene.

The invention provides a diagnostic kit for the detection of an antigen selected from an MPD5 antigen, a PV65 antigen, and a PV13 antigen comprising a container comprising at least one antibody wherein the at the least one antibody specifically binds to an epitope of a peptide selected from the group consisting of an MPD5 peptide, a PV65 peptide, and a PV13 peptide. The invention further provides the diagnostic kit further comprising a solid support, wherein said solid support is selected from the group consisting of wells of reaction trays, test tubes, polystyrene beads, strips, membranes and microparticles. The invention further provides the diagnostic kit further comprising a label, wherein said label is selected from the group consisting of enzymes, radioisotopes, fluorescent compounds and chemiluminescent compounds. The invention further provides the diagnostic kit that the enzymatic label is horseradish peroxidase. The invention further provides the diagnostic kit that further comprises a hapten and labeled anti-hapten system wherein the hapten is conjugated to a labeled murine monoclonal antibody.

The invention provides a method for detecting the presence of a peptide selected from the group consisting of an MPD5 peptide, a PV65 peptide, and a PV13 peptide in a biological sample comprising: a) contacting a biological sample with an antibody selected from the group consisting of anti-MPD5 antibody, anti-PV65 antibody, anti-PV13 antibody to form an antibody complex; b) contacting the antibody complex with a detection antibody so that the detection antibody binds to the soluble antibody complex; and c) detecting the presence of the detection antibody that bound to the antibody complex, thereby detecting the presence of the peptide in the sample. The invention further provides that the biological sample is a member selected from the group consisting of whole blood, serum, plasma, cerebrospinal fluid, saliva, urine, spinal fluid, synovial fluid, amniotic fluid and cranial fluid, and lymphocyte or cell culture supernatants.

The invention provides a method for monitoring the course of disease in a patient which comprises quantitatively determining in a first cell sample from the subject the presence of MPD5 a peptide selected from the group consisting of an MPD5 peptide, a PV65 peptide, and a PV13 peptide and comparing the amount so determined with the amount present in a second sample from the subject, such samples being taken at different points in time, a difference in the amounts determined being indicative of the course of disease.

The invention provides a method for monitoring the course of disease in an cancer patient subject which comprises obtaining a first sample from the subject; determining from the first sample at least one measure of a peptide selected from the group consisting of an MPD5 peptide, a PV65 peptide, and a PV13 peptide; at a different time, obtaining a second sample from the subject; determining from the second sample at least one measure of the peptide; wherein a difference in the measured peptide determined from the first sample and the second sample being indicative of the course of disease.

The invention provides a method of diagnosing a disease condition related to a disorder selected from the group consisting of viral infections, inflammation, autoimmune disease, and cancer in a patient comprising obtaining a blood sample from the patient; determining from the sample at least one measure of a peptide selected from the group consisting of an MPD5 peptide, a PV65 peptide, and a PV13 peptide; presenting such measure; and applying the measure of the peptide selectively as a diagnostic evaluation of a disease condition related to a disorder selected from the group consisting of viral infections, inflammation, autoimmune disease, and cancer.

BRIEF DESCRIPTION OF SEVERAL VIEWS OF THE DRAWINGS

The invention will be described in conjunction with the following drawings in which like reference numerals designate like elements and wherein:

FIG. 1. The novel PV-associated SEREX antigen, MPD5, is an unconventional antigen.

FIG. 2. The expression of MPD5 transcripts is elevated in tumors and PV.

FIG. 4. The novel tumor antigen PV65 (eIF-2α).

FIG. 5. The novel tumor antigen PV13 (protamine 2).

DETAILED DESCRIPTION OF THE INVENTION

Identification of Novel PV-Associated SEREX Antigens

Figure 1A:
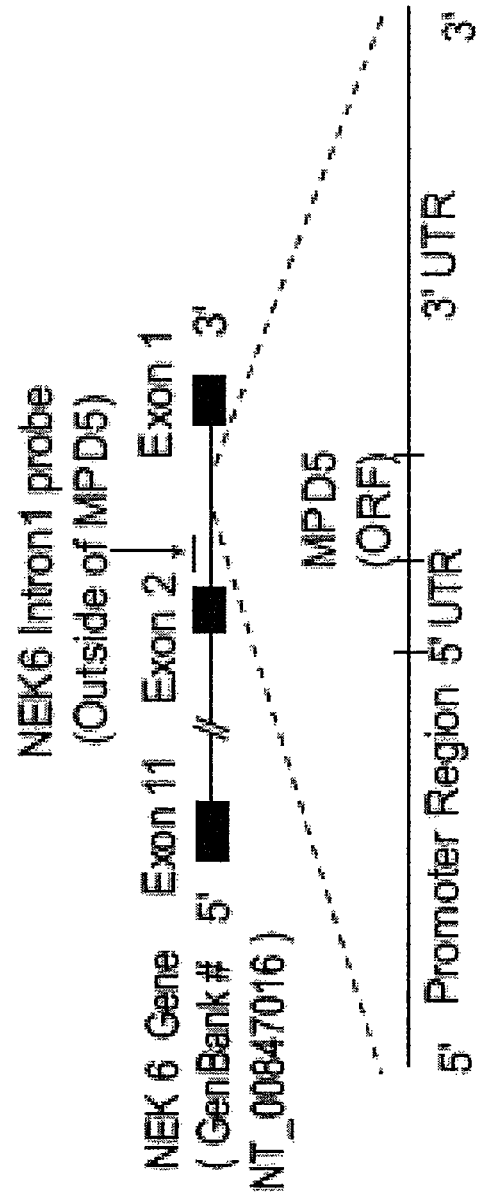
FIG. 1A. A schematic representation of the location of the unconventional antigen, MPD5, in the complementary (i.e., antisense) strand within the intron 1 region of the NEK6 (NIMA-6) gene (GenBank accession number: NT_00847016).

The inventor performed SEREX screening of a human allogeneic testis expression cDNA library using diluted sera collected from the patients with PV who responded to IFN-α therapy. The inventor chose sera from three patients with PV for cDNA library screening based on two criteria: (1) the patients' diseases had undergone remission, as judged by conversion from monoclonal to polyclonal hematopoiesis as determined by analyses of the patients platelets and granulocytes by transcriptional based X-chromosome inactivation assay (2) (not shown); and (2) improved blood counts (Liu et al., Discrimination of polycythemias and thrombocytoses by novel, simple, accurate clonality assays and comparison with PRV-1 expression and BFU-E response to erythropoietin, Blood 101(2003) 3294-3301. E. Lengfelder et al., Interferon alpha in the treatment of polycythemia vera, Ann Hematol 79(2000) 103-109.). Initial screening of 1×10$^6$λ recombinant phage clones led to identification of 15 positive clones (not shown). Subsequently, after several rounds of the purification of positive phage plaques and further confirmation on their antigen specificities, two independent cDNA clones were identified.

MPD5

The identification of novel unconventional antigen MPD5 is a part of the first such study in PV and other BCR-ABL negative MPDs (Xiong Z., E. Liu, Y. Yan, R. T. Silver, F. Yang, I. H. Chen, Y. Chen, S. Verstovsek, H. Wang, J. Prchal and X. F. Yang. 2006. An unconventional antigen translated by a novel internal ribosome entry site elicits antitumor humoral immune reactions. J. Immunol. 177:4907; Yang X et al., Processing sites are different in the generation of HLA-A2.1-restricted T cell reactive tumor antigen epitopes and viral epitopes. Intl. J. Immunopathol. Pharmacol. 19 (4), in press). Prior to the current report, whether unconventional cryptic antigens (Shastri N et al. 2002. Producing nature's genechips: the generation of peptides for display by MHC class I molecules. Annu. Rev. Immunol. 20:463) can elicit humoral immune responses has not been well defined. Our recent results on T cell antigen epitope of CML66 indicate that integrated humoral and T cell immune responses to SEREX antigens are truly tumor-specific. Of note, the results of our analysis employing the methods (Ng B et al. 2004. Increased noncanonical splicing of autoantigen transcripts provides the structural basis for expression of untolerized epitopes. J. Allergy Clin. Immunol. 114:1463.) suggest that protein sequences of MPD5 have a high potential to encode T cell antigen epitopes. Several new systems contribute to protein antigen presentation and co-stimulation, and shape the T cell responses including Qa-1 (Lu L et al. 2006. The immunoregulatory effects of Qa-1. Immunol. Rev. 212:51), and ICOS-B7RP-1. The question of whether these new systems participate in elicitation of T cell responses to unconventional protein antigens, such as MPD5, remains unknown.

The inventor demonstrated that upregulation of untolerized antigen structure via alternative splicing is a novel mechanism in generating the immunogenicity of tumor antigens (Yan Y., L. Phan, F. Yang, M. Talpaz, Y. Yang, Z. Xiong, B. Ng, N. A. Timchenko, C. J. Wu, J. Ritz, H. Wang and X. F. Yang. 2004. A novel mechanism of alternative promoter and splicing regulates the epitope generation of tumor antigen CML66-L. J. Immunol. 172:651). The current study on MPD5 suggests that overexpression of "intron antigens" in tumor cells is one of the mechanisms involved in eliciting immune responses. In addition, overexpressed antigens must have untolerized antigen epitopes partially by splicing (Yang F et al. 2006. Model of stimulation-responsive splicing and strategies in identification of immunogenic isoforms of tumor antigens and autoantigens. Clin. Immunol. 121:121). Furthermore, overexpressed antigens must access the antigen presentation pathway and immune system by the following mechanisms (3): (1) releasing from damaged tumor cells followed by cross-presentation; (Liu et al. 2003. Discrimination of polycythemias and thrombocytoses by novel, simple, accurate clonality assays and comparison with PRV-1 expression and BFU-E response to erythropoietin. Blood 101:3294) translocating across the intracellular membranes and entering exosome for the MHC class II antigen presentation pathway. Notwithstanding, the correlation between antigen-specific IgG immune responses and remission in PV patients (Lengfelder E et al. 2000. Interferon alpha in the treatment of polycythemia vera. Ann. Hematol. 79:103) indicates that immune responses mediated by unconventional antigen(s) may contribute to MPD remission (Yang F. and X. F. Yang. 2005. New concepts in tumor antigens: their significance in future immunotherapies for tumors. Cell Mol. Immunol. 2:331). Homo sapiens myeloproliferative disease-associated SEREX antigen mRNA was deposited with GenBank, accession number AY611627.

PV-Associated SEREX Antigen MPD5 is an Unconventional Antigen

SEREX screening of human testis expression cDNA library was performed using diluted sera collected from 3 PV patients who responded to IFN-α therapy; these patients were selected, based on two criteria: (1) the patients' diseases had undergone remission, as judged by conversion from monoclonal to polyclonal hematopoiesis (2) (not shown); and (2) improved blood counts (1,2). A screening of $1 \times 10^6 \lambda$ phage clones led to the identification of two identical clones.

Figure 1B:
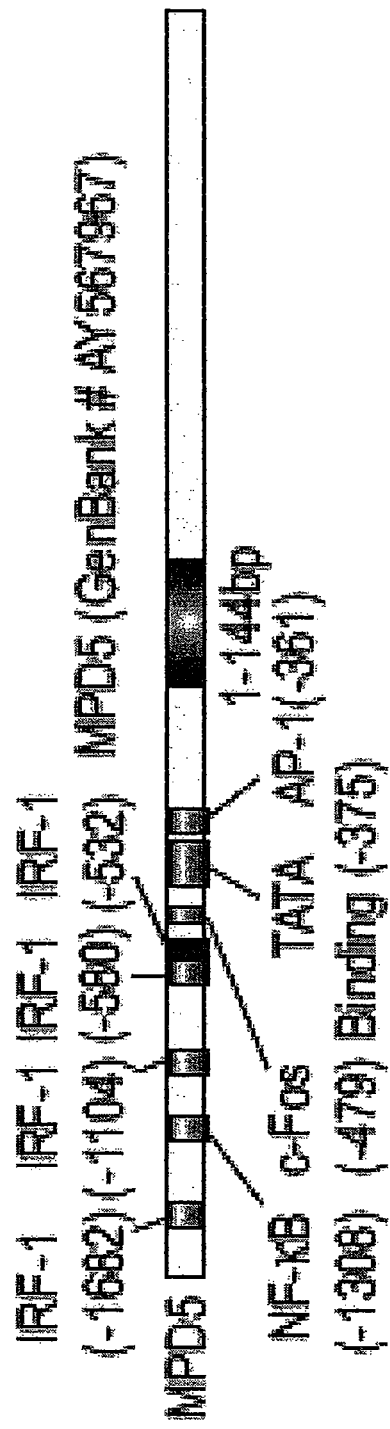
FIG. 1B. The structure of MPD5 promoter and the structure of MPD5 mRNA transcript. MPD5 has an ORF of 144 bp (GenBank accession number: AY567967). Four interferon regulatory factor 1 (IRF-1) binding sites—including NF-KB, AP1, and other transcription factor binding sites—were found in the 2 kb region of the MPD5 promoter. These results suggest that MPD5 transcription may be regulated by interferon-α stimulation.

The open reading frame (ORF) in the clone (1517 bp) encoded 47 amino acids with the molecular size of 5 kD, herein referred to as MPD5 (GenBank accession: AY567967). The antisense sequence of MPD5 was identical to a 5.1 kb cDNA clone (GenBank accession: AL832574; not shown). Both MPD5 and the 5.1 kb clone were located in intron 1 of NEK6 (i.e., NIMA [never in mitosis gene a]-related kinase 6) (GenBank accession: NT_008470.16). A member of the serine/threonine kinase family, NEK6 is a homolog of histone H3 kinase, which is required for cell cycle progression through mitosis. The 5.1 kb cDNA was encoded on the same strand as the sense-strand of the NEK6 gene; whereas, whereas MPD5 was encoded in the complementary strand within the intron 1 region of the NEK6 gene (FIG. 1A). Notably, there were no long ORFs found in the sense and complementary sequences of this 5.1 kb cDNA clone. The function of the 5.1 kb cDNA is unclear; however, our identification of the MPD5 and 5.1 kb clones in the cDNA library suggest that the region in intron 1 of NEK6 is transcriptionally active on both strands. This argument is further supported by our in silico analysis on the promoter regions for MPD5 transcription, which showed several transcription factors including interferon regulatory factor-1 (IRF-1) binding sites (14) and sites for NF-κB (15), c-fos, and AP-1 (FIG. 1B).

Figure 1C:
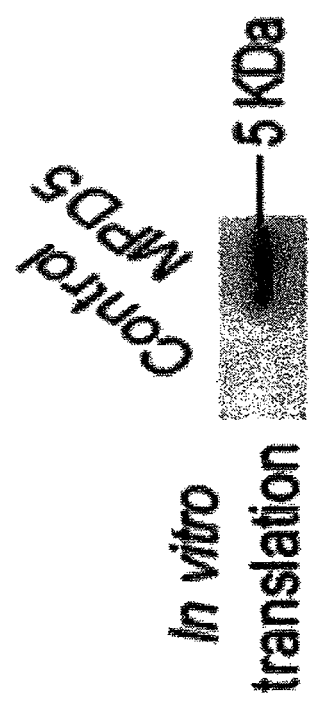
FIG. 1C. The in vitro transcription and translation product of MPD5.

The 5 kD ORF of MPD5 was confirmed by TNT, depicted in FIG. 1C. The MPD5 protein sequence (FIG. 1D) was not identical to sequences in the NCBI databases or the SEREX database, although a segment in the 3'untranslated region of MPD5 showed homology to a SEREX clone HOM-HD2-117 (the SEREX database, not shown). The following features support our contention that MPD5 is a human protein (FIG. 1D): (1) the start codon and the surrounding sequence contain the Kozak consensus for optimal translation(16); (2) the frequencies of amino acid (a.a.) codon usage, including a.a. residues with multiple codons, are identical to those used in human proteins; (3) analysis using the NCBI conserved domain database demonstrates that the a.a. sequence of MPD5—specifically, aa 7 to aa 43—has a high homology (i.e., 49%) with the GTPase Dbl-homologous (DH) domain (Protein family database: pfam.wustl.edu/, pfam00621); and (4) the MPD5 sequence encoded several sites from various posttranslational modifications, including cyclin interaction, protein kinase A phosphorylation site, and N-glycosylation site. Cumulatively, these MPD5 features correspond to the characteristics previously reported in short protein-encoding ORFs(17). Furthermore, in the Kyte-Doolittle hydrophilicity plot of the MPD5 peptide (FIG. 1E), the two hydrophilic regions suggest the potential for antibody binding epitopes (10).

The Expression of MPD5 Transcripts is Elevated in Tumors and PV

Figure 2A:
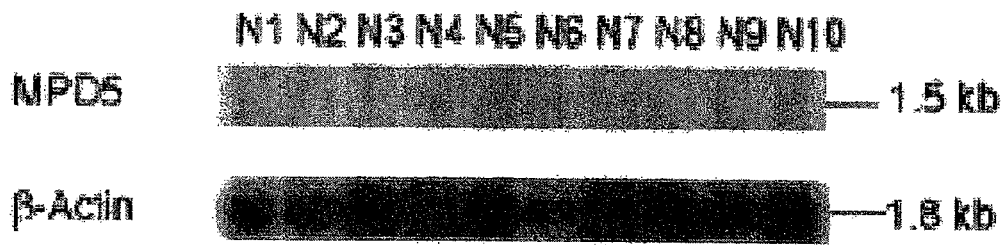
FIG. 2A. The expression of MPD5 transcripts in normal tissues. Lanes N1 to N10 indicate various normal tissues in the brain (N1), liver (N2), placenta (N3), small intestine (N4), colon (N5), thymus (N6), spleen (N7), prostate (N8), testis (N9), and ovary (N10), respectively. The transcript sizes are indicated as kilobases (kb).
Figure 2B:
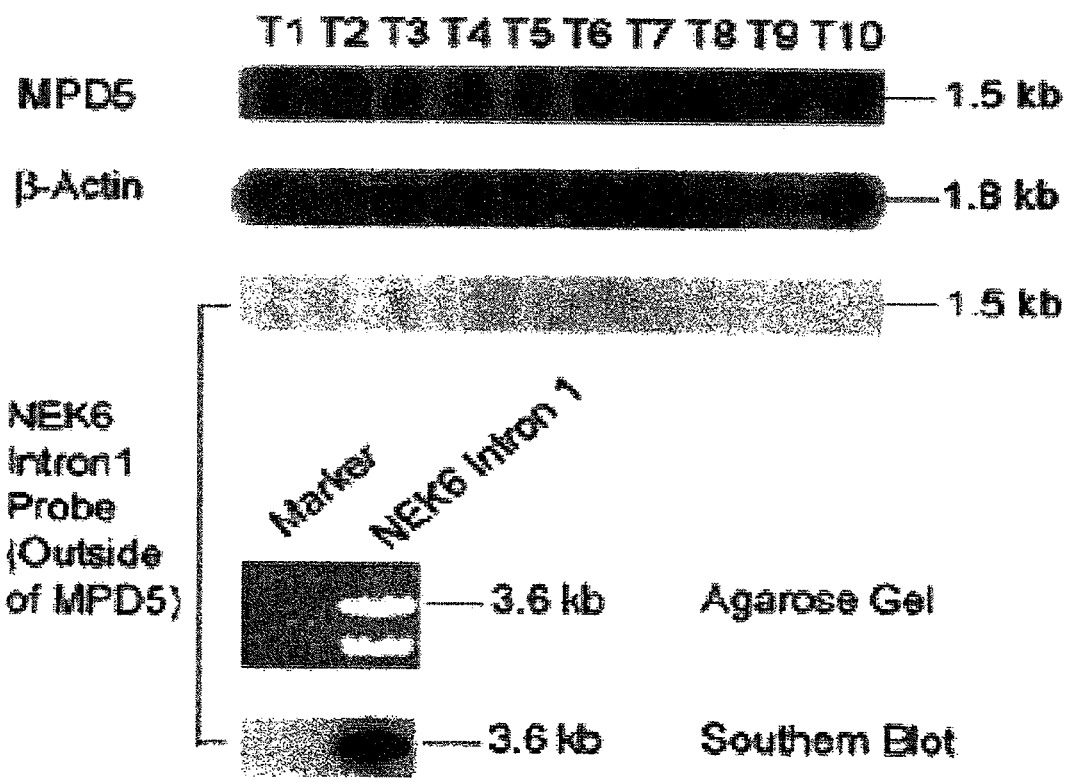
FIG. 2B. Expression of MPD5 transcripts in tumor cells, as detected by Northern blot. Lanes T1 to T10 indicate various tumor cells in acute T cell leukemia (Jurkat cells) (T1), Burkitt's lymphoma (CA46) (T2), breast cancer (MDA-MD-453) (T3), Burkitt's lymphoma (Namalwa) (T4), epidermal carcinoma (A-431) (T5), uterine carcinoma (MES-SA) (T6), Burkitt's lymphoma (Raji) (T7), osteosarcoma (MG-63) (T8), histiocytic lymphoma (U-937) (T9), and cervical adenocarcinoma (Hela S3) (T10), respectively. In the lower panel, the specificity of the NEK6 intron 1 probe (outside of MPD5) was confirmed by Southern blot of an agarose gel analyzing a NEK6 intron 1 fragment that was located outside the MPD5 region and had no overlap with MPD5.

Applying our reported strategy, the Northern blot shows that the expression of MPD5 in 10 normal tissues (e.g., the brain [N1], colon [N5], prostate [N8], testes [N9], and ovary [N10], etc.) was negligible (FIG. 2A). However, MPD5 expression was significantly upregulated in a variety of tumor cells (FIG. 2B), including acute T cell leukemia (T1), Burkitt's lymphoma (T2, T4, and T7), uterine carcinoma (T6), osteosarcoma (T8), histiocytic lymphoma (T9), and cervical adenocarcinoma (T10). Since the MPD5 is located on the antisense strand of intron 1 within the NEK6 gene (FIG. 1A), the Northern hybridization signals in tumor tissues (FIG. 2B) resulting from hybridization might have been attributable to contaminated genomic DNA in the RNA preparation. In order to exclude this possibility, the inventor generated a 3.6 kb NEK6 intron 1 (intron 1) region (the lower panel in FIG. 2B) that has no overlap with the MPD5 region (FIG. 1A). Hybridization of the Northern blot with the intron 1 probe did not yield any observable signals, suggesting that the MPD5 signals (FIG. 2B) did not result from contaminated genomic DNA. In contrast, the Southern blot hybridization on agarose gel—used to analyze the intron 1 fragment with a special intron 1 probe—showed a strong signal (lower panel, FIG. 2B). This suggests that the intron 1 probe is capable of detecting potentially contaminated genomic DNA in tumor tissue RNA preparations (FIG. 2B). In sum, our findings indicate the detection of upregulated MPD5 expression in tumor cells.

Figure 2C:
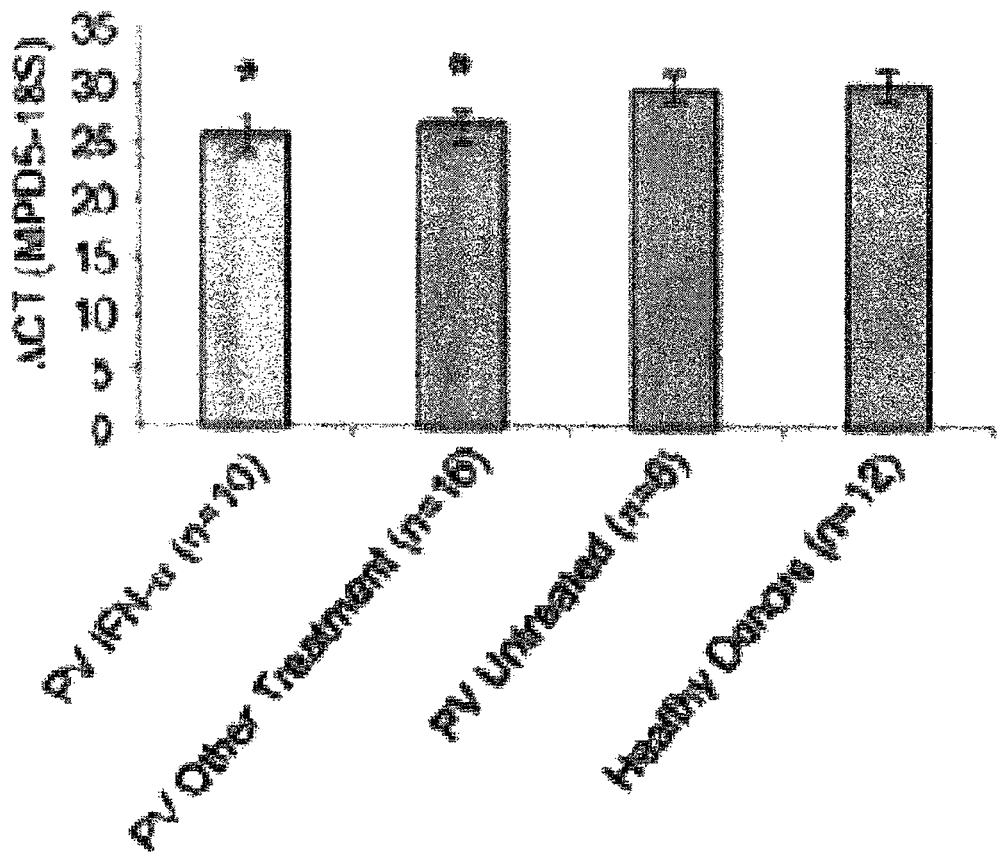
FIG. 2C. The expression of MPD5 transcripts in the granulocytes from PV patients and healthy donors, as detected by quantitative RT-PCR. The expression levels of MPD5 transcripts are expressed as the ΔCT (MPD5-18S). Low ΔCT values indicate higher expression of the specific gene. The groups, whose expression of MPD5 transcripts is statistically different from that of healthy donors ($p<0.05$), are marked with an *.

The inventor subsequently examined MPD5 expression in granulocytes via quantitative PCR, with 18S as the normalizer, to calculate MPD5 expression levels in PV patients receiving IFN-α therapy (n=10), PV patients receiving other treatments (Hydroxyurea, Imatinib mesylate, Anagrelide, or Phlebotomy; n=16), PV patients receiving no treatment (n=6), and healthy donors (n=12). Low ΔCT values indicate higher expression of a specific gene. As shown in FIG. 2C, MPD5 was not expressed in the granulocytes of healthy donors (mean±2× standard deviations [2SD] of the ΔCT [MPD5-18S]=28.5-31.5). Conversely, MPD5 expression levels in the granulocytes of PV patients receiving IFN-α (mean±2SD of the ΔCT [MPD5-18S]=24-27) and those of PV patients receiving other treatments (mean±2SD of the ΔCT [MPD5-18S]=25-27.5) were higher than those of untreated PV patients or healthy donors (mean±2SD of the ΔCT [MPD5-18S]=28.5-31.5) (p<0.05). Notwithstanding, MPD5 expression levels in the granulocytes of PV patients receiving IFN-α were not higher than those of patients receiving other treatments (p>0.05). It is also noteworthy that the discrepancy between the numbers of patients and healthy controls in FIG. 2C and that in FIG. 3 resulted from the limited volumes of some blood samples, in which high quality RNAs could not be prepared but the sera could be prepared for performing the experiments presented in FIG. 3.

Figure 2D:
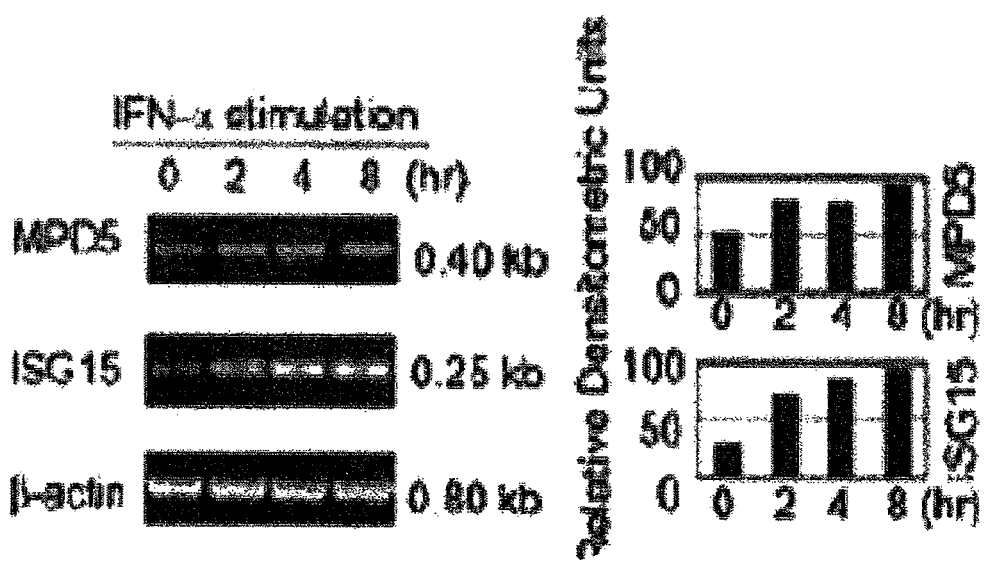
FIG. 2D. The MPD5 expression in K562 cells stimulated with IFN-α, as detected by semi-quantitative RT-PCR (the left panel). RT-PCR of β-actin served as a housekeeping control for IFN-α stimulation. The RT-PCR of ISG15 was used as a positive control for IFN-α stimulation. In the right panel, the densitometric units were calculated by normalizing the densities of the PCR products of MPD5 and ISG15 with those of β-actin in the same sample.

The inventor further hypothesized that MPD5 expression in tumors can be upregulated either by direct IFN-α stimulation associated with IFN-α therapy or, potentially, through the activation of IRF-1 using other therapies (Romeo G et al. 2002. IRF-1 as a negative regulator of cell proliferation. J. Interferon Cytokine Res. 22:39). This hypothesis was supported by our in silico mapping of IRF-1 binding sites (G(A) AAAG/CT/CGAAAG/CT/C)(SEQ ID NO: 18) in the MPD5 promoter region (FIG. 1B). In FIG. 2D, the results of semi-quantitative RT-PCR showed that MPD5 transcripts in K562 myeloid leukemia cells were upregulated by IFN-α stimulation, even though the upregulation scale (nearly 100%) of MPD5 was not as high as that (200%) of IFN-α-stimulated gene-15 (ISG15) (FIG. 2D), which was employed as a positive control for the IFN-α-stimulated genes. Of note, the amplification of MPD5 transcripts by RT-PCR did not result from genomic DNA potentially contaminated in RNA prepared from stimulated K562 cells; this conclusion is based on the following: (1) the RNA were treated with RNase-Free DNase before reverse transcription and the PCR involving primers located in the NEK6 intron 1 region outside of MPD5 did not result in any amplified products. However, the results suggest that a transcriptional mechanism in K562 cells could be one of the regulatory programs implicated in the upregulation of MPD5 expression induced by IFN-α or IRF-1 activation associated with other therapies. Of note, the limited number of PV patients prevented similar IFN-α stimulation performed with PV cells.

Figures 1D, 1E:
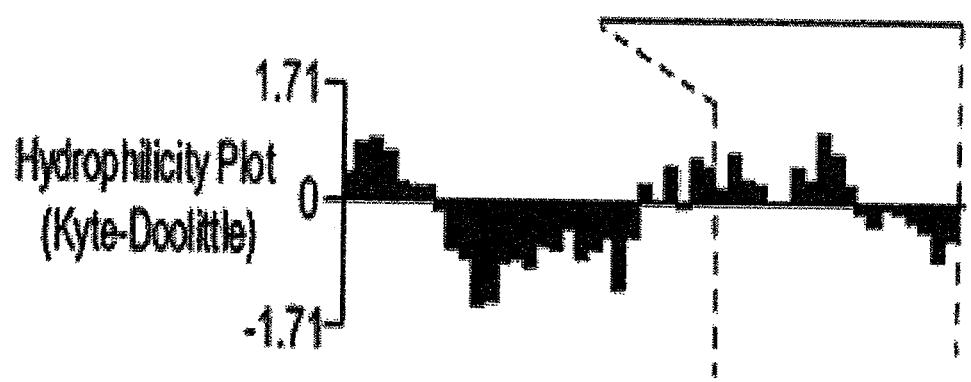
FIG. 1D. The protein sequence of MPD5 (SEQ ID NO: 2).
FIG. 1E. The hydrophilicity index plot of MPD5, analyzed by the Kyte-Doolittle method, suggests that there are hydrophilic regions within the N-terminal and C-terminal regions of MPD5.
Figure 3:
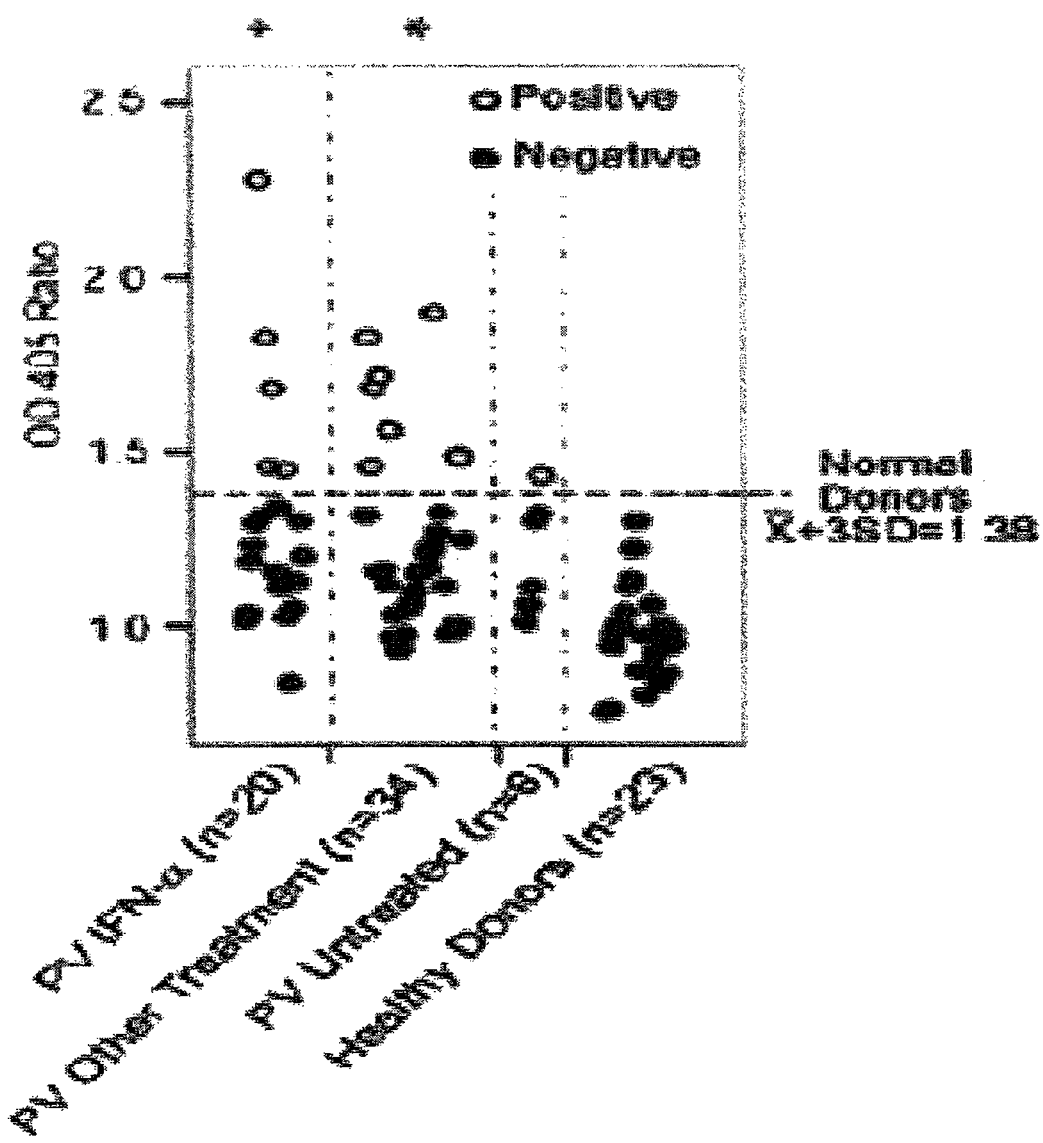
FIG. 3. MPD5 peptide specifically reacts to sera from PV patients responding to therapies. IgG antibody responses to the C-terminal antigenic epitope (from aa 30 to aa 47) of MPD5 were detected by peptide ELISA. These experiments were repeated three times, and representative results are shown. The mean plus three standard deviations (SD) of the OD405 peptide ratios over the coating control (derived from 23 healthy donors) was calculated as the upper limit of the normal range of MPD5 peptide antibody responses (the mean+3SD=1.38). The groups with detection rates of IgG antibody responses to MPD5 peptide that are statistically higher than those of healthy donors (the chi-square goodness-of-fit test; p<0.05) are marked with an asterisk *.

MPD5 Peptide Specifically Reacts to Sera from PV Patients who Experienced Therapeutic-Induced Remission, but Not Sera from Untreated Patients or Healthy Donors To further verify whether MPD5 antigen epitope is immunogenic in vivo, an MPD5 peptide was synthesized according to the amino acid sequence of the second antigen epitope of MPD5, from aa 30 to aa 47 (FIGS. 1D and E). MPD5 peptide-specific IgG antibody responses, shown as the OD405 ratio (OD405 MPD5 peptide/OD405 coating control) (FIG. 3), as the inventor previously reported (18), were negligible in the serum samples of all 23 healthy donors [the mean+ 3SD=1.38]. Thus, in FIG. 3, an OD405 ratio higher than 1.38 is considered positive for anti-MPD5 IgG antibody responses. As summarized in FIG. 3, MPD5 epitope-specific IgG antibody responses were detected in serum samples from 5 out of 20 (25%) PV patients receiving IFN-α therapy, and in 7 out of 34 serum samples (21%) from PV patients receiving other therapies (FIG. 3). Of note, a good correlation existed between increased MPD5 expression in granulocytes, as detected by quantitative PCR, and the specific antibody responses detected by ELISA in PV patients receiving IFN-α and other therapies. These results suggest that the antigenic epitope in MPD5 protein, which is naturally translated, was immunogenic in the PV patients receiving therapy. It is noteworthy that serum results obtained with the MPD5 ELISA corresponded well with those achieved through the phage plaque assay (not shown).

PV-Associated SEREX Antigens PV65 and PV13

By applying SEREX, the inventor has identified two novel antigens that are capable of eliciting potent humoral immune responses associated with PV remission. This is a part of the first such a study in BCR-ABL negative MPD (S. Gilbert, Current management in polycythemia vera, Semin Hematol 38 (2001) 25-28; Xiong, E. Liu, Y. Yan, R. T. Silver, F. Yang, 1. H. Chen, Y. Chen, S. Verstovsek, H. Wang, 1. Prchal, X. F. Yang, An unconventional antigen translated by a novel internal ribosome entry site elicits antitumor humoral immune reactions, J Immunol 177(2006) 4907-4916). The analyses showed that these novel tumor antigens are not identical to any hematologic malignancy antigens identified previously with SEREX (17) or other approaches (F. Yang, X. F. Yang, New concepts in tumor antigens: their significance in future immunotherapies for tumors, Cell Mol Immunol 2 (2005) 331-341; Novellino, C. Castelli, G. Parmiani, A listing of human tumor antigens recognized by T cells: March 2004 update, Cancer Immunol Immunother (2004)). These antigens were identified using sera from female patients, however, the chromosomal locations of these gene loci (PV65 at 3q25, and PV13 at 16p13.2) showed that they were encoded by genes located in autosomal chromosomes, but not in the male-specific Y chromosome (Simpson, D. Scott, P. Chandler, The male-specific histocompatibility antigen, H-Y: a history of transplantation, immune response genes, sex determination and expression cloning, Annu Rev Immunol 15(1997) 39-61), suggesting that anti-tumor immune reactions in PV patients might be partially mediated by the novel self-tumor antigens identified in this study.

IFN-α-induced, double-stranded (ds) RNA-activated protein kinase (PKR) is a key mediator of the antiviral and anti-proliferative effects of IFN (44). A known physiological substrate of PKR activity is the a subunit of the eukaryotic translation initiation factor eIF-2α (C. Patel, G. C. Sen, PACT, a protein activator of the interferon-induced protein kinase, PKR, Embo J 17(1998) 4379-4390.). As shown for other IFN-α inducible genes (E. C. Baechler et al. Interferon-inducible gene expression signature in peripheral blood cells of patients with severe lupus, Proc Natl Acad Sci USA 100 (2003) 2610-2615), the inventor found that increased phosphorylation of eIF-2α, via IFN-α stimulation or activation of IRF-1 (Matikainen, A. et al., Regulation of IRF and STAT gene expression byretinoic acid, Leuk Lymphoma 30 (1998) 63-71; M. K. Chelbi-alix, et al., Arsenic enhances the activation of Stat 1 by interferon gamma leading to synergistic expression of IRF-1, Oncogene 22(2003) 9121-9130) and PKR potentially associated with other therapies, might enhance their abilities to elicit immune responses in patients. Posttranslational modification, including protein phosphorylation has been shown to be an important pathway for self-proteins to gain the immunogenicity (Utz, T. et al., Death, auto antigen modifications, and tolerance, Arthritis Res 2 (2000) 101-114.).

The inventor showed that upregulation via alternative splicing is a novel mechanism for the generation of the immunogenicity of self-tumor antigen CML66-L (Yan, L. et al., A novel mechanism of alternative promoter and splicing regulates the epitope generation of tumor antigen CML66-L, J Immunol 172 (2004) 651-660.). Our results further demonstrated here that PV13 is upregulated in tumor cells, suggesting that overexpression of PV13 antigen in tumor cells is one of the mechanisms for eliciting immune reactions. A recent study reported that PV13 (protamine 2) is a tumor antigen (MA-CT-1) associated with a subgroup of patients with prostate cancer (4.6%)(L. H. Hoeppner et al., Humoral immune responses to testis antigens in sera from patients with prostate cancer, Cancer Immun 6 (2006)). Cumulatively, our results and others' suggest that PVL3 (protamine 2) may be a broadly immunogenic tumor antigen, which corresponds well with our results on PV13 expression in various tumor cells. As suggested previously, lower rates of antibody reactions to PV13 in patients with PV and prostate cancer are similar to the expression rates of cancer testis antigens (2%-31%)(M. J. Scanlan, D. Jager, Challenges to the development of antigen-specific breast cancer vaccines, Breast Cancer Res 3(2001) 95-98.), which may result in the status of methylation-demethylation of tumor antigen promoters in tumor cells.

Correlation of antigen-specific IgG immune reactions with remission in PV patients suggests that immune reactions mediated by these novel antigens contributes to the MPD remission. Most recently, a gain-of-function acquired somatic mutation (V617F) of the tyrosine kinase JAK2 has been identified in most patients with PV and other MPDs (R. L. Levine et al. Activating mutation in the tyrosine kinase JAK in polycythemia vera, essential thrombocythemia, and myeloid metaplasia with myelofibrosis, Cancer Cell 7 (2005) 387-397.). The important issue of how the activating mutation of JAK may modulate the expression of tumor antigens and anti-tumor immune reactions is under investigation (Verma, S et al., Jak family of kinases in cancer, Cancer Metastasis Rev 22(2003) 423-434.). Taken together, our results suggest that novel PV associated tumor antigens may elicit anti-tumor humoral immune reactions in patients with PV. This provides new insights into the mechanism underlying the regulation of the self-antigen repertoire in eliciting anti-tumor immune reactions in patients with myeloproliferative diseases and suggests their potential as the targets of novel immunotherapy.

PV-Associated SEREX Tumor Antigen PV65

Figure 4A:
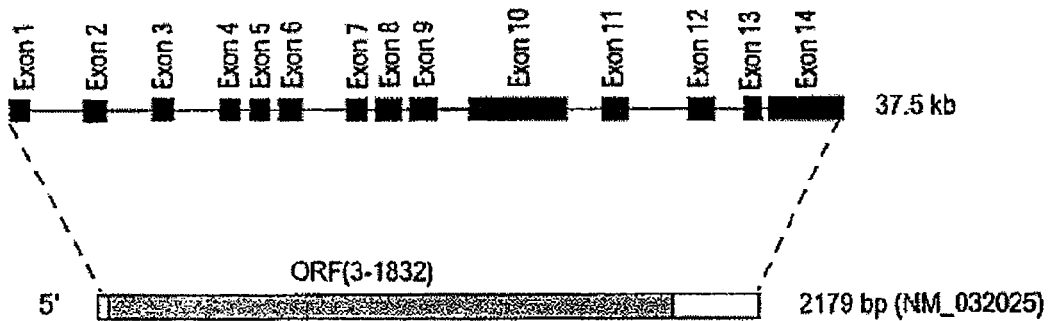
FIG. 4A. Schematic representation of the genomic structure, mRNA, and protein structure of tumor antigen PV65 (eIF-2α, GenBank accession number: NM_032025).
Figure 4B:
FIG. 4B. The expression of PV65 transcripts in normal tissues detected by Northern blot. The lanes N1 to N10 indicate various normal tissues in the order of brain (N1), liver (N2), placenta (N3), small intestine (N4), colon (N5), thymus (N6), spleen (N7), prostate (N8), testis (N9), and ovary (N10), respectively. The hybridization analyses of the normal tissue and tumor cell expression (BD Clontech) with 32P-Labelled specific probes, as indicated, were performed, respectively. The transcript sizes are indicated with kilobases (kb).
Figure 4C:
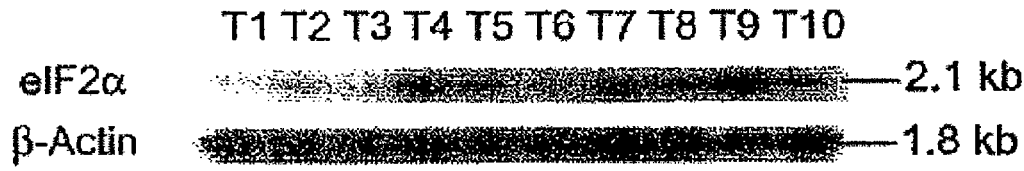
FIG. 4C. The expression of PV65 transcripts in tumor cells detected by Northern blot. The lanes T1 to T10 indicate various tumor cells in the order of acute T cell leukemia (Jurkat cells) (T1), Burkitt's lymphoma (CA46) (TI), breast cancer (MDA-MD-453) (T3), Burkitt's lymphoma (Namalwa) (T4), epidermal carcinoma (A-431) (T5), uterine carcinoma (MES-SA) (T6), Burkitt's lymphoma (Raji) (T7), osteosarcoma (MG-63) (T8), histiocytic lymphoma (U-937) (T9), and cervical adenocarcinoma (Hela S3) (T10), respectively.
Figure 4D:
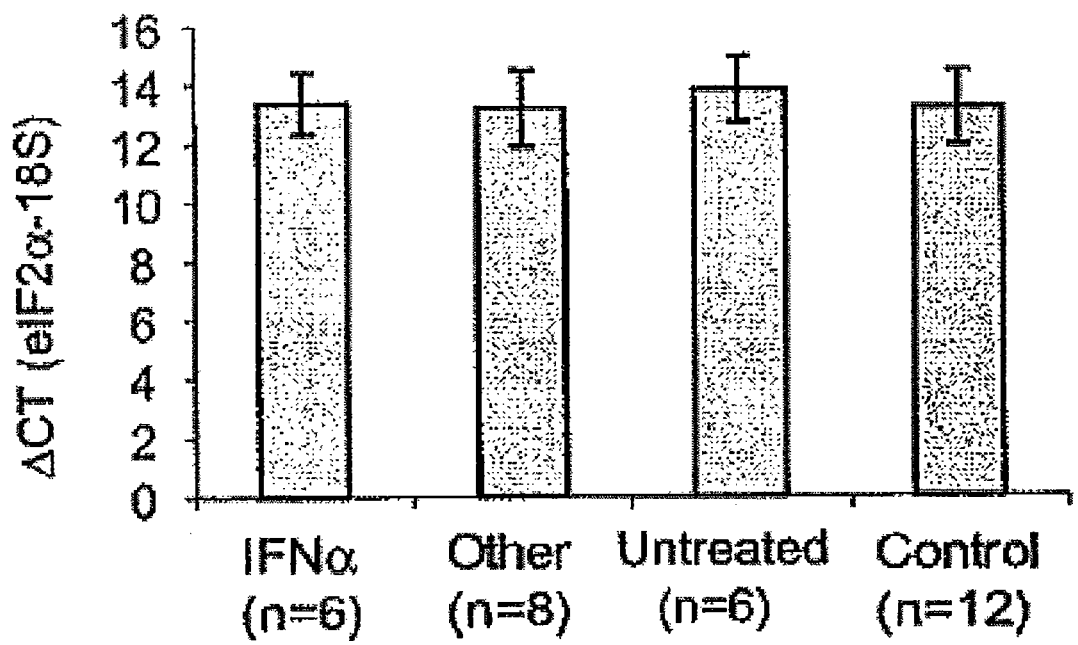
FIG. 4D. The expression of PV65 transcripts in the granulocytes from PV patients and healthy donors detected by quantitative RT-PCR. The expression levels of PV65 transcripts are expressed as the deltaCT (PV65-18S). Low deltaCT values indicate higher expression of the specific gene. The experiments were repeated for three times. The mean and standard deviation for each group were calculated.

The DNA analysis of the first clone with a 619 bp insert showed that it was identical to eukaryotic translation initiation factor 2ex (eIF-2ex) (GenBank accession: NM_032025) (28). The eIF-2ex is a 585 aa protein with a molecular size of 65 kD (FIG. 4A), which was thus referred to as PV65 (C. Koumenis et al., Regulation of protein synthesis by hypoxia via activation of the endoplasmic reticulum kinase PERK and phosphorylation of the translation initiation factor eIF2alpha, Mol Cell Biol 22(2002) 7405-7416.). Furthermore, the Northern blot showed the expression of PV65 was low in normal tissues (FIG. 4B), but was significantly upregulated in some tumor cells, i.e. Burkitt's lymphoma (T4, and TI ), osteosarcoma (T8), and histocytic lymphoma (T9) (FIG. 4C) in comparison to that of Bactin housekeeping gene control. Previous reports and the data deposited in the NCBI-Unigene website in NCBI-GenBank showed that the PV65 expression was increased in some solid tumors including mammary tumors (B. Raught et al., Expression of a translationally regulated, dominant-negative CCAAT/enhancer-binding protein beta isoform and up-regulation of the eukaryotic translation initiation factor 2alpha are correlated with neoplastic transformation of mammary epithelial cells, Cancer Res 56(1996) 4382-4386), melanomas, and colon cancers (I. Rosenwald et al., Expression of translation initiation factor eIF-2α is increased in benign and malignant melanocytic and colonic epithelial neoplasms, Cancer 98(2003) 1080-1088), compared to normal tissues, suggesting that PV65 expression might be modulated in patients with PV. To test this possibility, the inventor performed quantitative PCR assay in measuring PV65 expression in granulocytes from patients with PV. As shown in FIG. 4D, PV65 expression (the CT (PV65-18S)) in patients with PV was not significantly higher than that in healthy donor controls ($p<0.05$), suggesting that the increased immunogenicity of PV65 in patients with PV might not be due to the higher expression of PV65 in granulocytes in patients with PV. Of note, this expression pattern of PV65 is not unique since a previous study also reported that a solid tumor associated gene I (STAG/PMEPA1) is upregulated in some solid tumors but not in leukemia samples (K. Rae et al., Characterization of a novel gene, STAG1IPMEPA1, upregulated in renal cell carcinoma and other solid tumors, Mol Carcinog 32(2001) 44-53.). It is also noteworthy that the discrepancy between the numbers of patients and healthy controls in FIG. 4D and that in FIG. 4F resulted from the limited volumes of some blood samples, in which high quality RNAs could not be prepared but the sera could be prepared for performing the experiments presented in FIG. 4F.

Figure 4E:
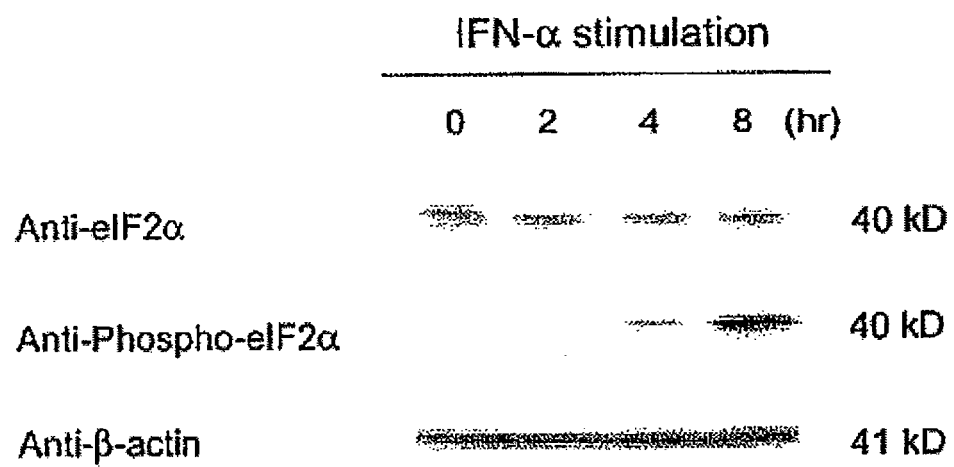
FIG. 4E. Western blot analyses of PV65 protein and phosphorylated PV65 protein in K562 myeloid leukemia cells. The expression levels of PV65 protein and phosphorylated PV65 protein in K562 cells at 0, 2, 4, and 8 hours after stimulation by IFN-α were assayed with Western blots using anti-PV65 and antiphosphorylated PV65, respectively. The Western blot analysis for the house keeping protein control β-actin was also performed using anti-β-actin as protein loading control.
Figure 4F:
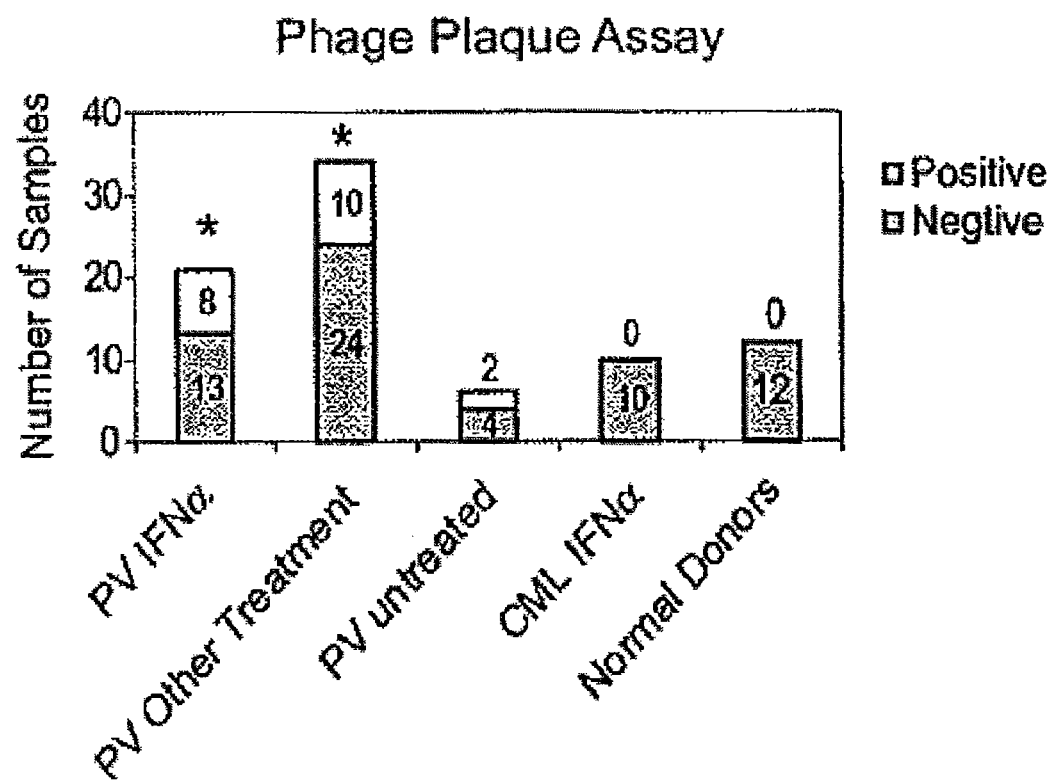
FIG. 4F. The IgG antibody reactions to the tumor antigen PV65 detected by phage plaque assay. The detection rates in each group are presented with the empty column as the positive (on the top) and the solid column as the negative (on the bottom). The experiments were repeated for three times. The representative results are shown. The groups, whose detection rates of the IgG antibody reactions to PV65 are statistically higher than that of healthy donors (the Chi-Square Goodness of-Fit Test; p<0.05), are marked with *.

Furthermore, since phosphorylation may increase the immunogenicity of the proteins (Utz et al., Death, auto antigen modifications, and tolerance, Arthritis Res 2(2000) 101-114.), the inventor tested the possibility whether PV65 can be phosphorylated by RNA-dependent protein kinase PKR (E. Meurs et al., Molecular cloning and characterization of the human double-stranded RNA-activated protein kinase induced by interferon, Cell 62(1990) 379-390.) activated via IFN-α stimulation in cultured K562 myeloid leukemia cells. Since there are no cultured PV cell lines available, using K562 myeloid leukemia cells due to the similarity among myeloproliferative diseases in our study was well justified. By using anti-PV65 (eIF-2α) antibody and anti-phosphorylated PV65 (eIF-2α) antibody to perform Western blots, as shown in FIG. 4E, the results showed that IFN-α stimulation did not significantly upregulate the expression of PV65 protein in myeloid leukemia cells, which corresponded well to that of PV65 expression in granulocytes in patients with PV detected by quantitative PCR (FIG. 4D). Interestingly, IFN-α stimulation significantly promoted its phosphorylation of PV65 (FIG. 1E), presumably via PKR (E. Meurs et al., Molecular cloning and characterization of the human double-stranded RNA-activated protein kinase induced by interferon, Cell 62(1990) 379-390.), which was also demonstrated in hematopoietic cells (D. I. Dimitrova et al., Lentivirus-mediated transduction of PKR into CD34(+) hematopoietic stem cells inhibits HIV-1 replication in differentiated T cell progeny, J Interferon Cytokine Res 25(2005) 345-360.). Thus, this result shown in FIG. 4E required no confirmation in PV cells. These results also suggested that the immunogenicity of the antigen PV65 might be associated with its critical role in IFN-α-induced inhibition of tumor growth and the phosphorylation of PV65. The results from phage plaque assay with the sera of three PV patients used in SEREX screening, showed that the serum sample from one patient recognized both of the two PV associated antigens, sera from two patients recognized one antigen, respectively, either PV65 or PV13 (data not shown). In addition, as shown in FIG. 4F, anti-PV65 IgG antibodies were not detected in any of the serum samples from 12 healthy donors, suggesting that PV65 was an authentic tumor-associated antigen. In contrast, anti-PV65 IgG antibodies were detected in eight out of 21 serum samples (38.1%) from PV patients receiving IFN-α therapy and also detected in 10 out of 34 serum samples (29.4%) from PV patients receiving other treatments. The detection rates of anti-PV65 IgG antibodies in both groups of PV patients were significantly higher than that of healthy donors (p.<0.05). Of note, anti-PV65 IgG antibodies were detected in two out of six patients with PV who have not received any treatment. Because of the limited number in this group, it was difficult to have a statistical comparison between the untreated group of PV patients and the two groups of PV patients receiving IFN-a and other therapies in detection of anti-PV65 IgG antibodies. Our previous reports on the identification of the novel tumor antigens CML66L (F. Yang, et al., CML66, a broadly immunogenic tumor antigen, elicits a humoral immune response associated with remission of chronic myelogenous leukemia, Proc Natl Acad Sci USA 98(2001) 7492-7497.) and CML28 (F. Yang et al., CML28 is a broadly immunogenic antigen, which is overexpressed in tumor cells, Cancer Res 62(2002) 5517-5522.) suggested that the immunogenicity of the antigens CML66L and CML28 was enhanced in IFN-a responders. The inventor also noticed that the detection rates of anti-PV65 antibody responses (FIG. 4F) in PV patients receiving IFN-α were higher than that in PV patients receiving other treatment. However, there were no statistical differences between these two groups of PV patients in their reactions to these novel antigens (p<0.05). Furthermore, in comparison to patients with PV, IgG antibody reactions to PV65 were not detected in ten patients with CML who received IFN-α treatment (p<0.05), suggesting that humoral reactions to PV65 might play a specific role in patients with PV. However, future extensive studies may be needed to verify this finding. Finally, there were no significant differences in the detection of IgG antibody reactions to PV65 among the PV patients receiving the therapeutics other than IFN-α (not shown). Taken together, the anti-PV65 IgG antibody reactions were detected in a fraction of patients with PV who received IFN-α and other therapies. Of note, the phage plaque assay used in this study does not detect non-phosphorylated proteins. Thus, some humoral immune reactions directed against phosphorylated PV65 might be missed out.

PV-Associated SEREX Tumor Antigen PV13 (Protamine 2)

Figure 5A:
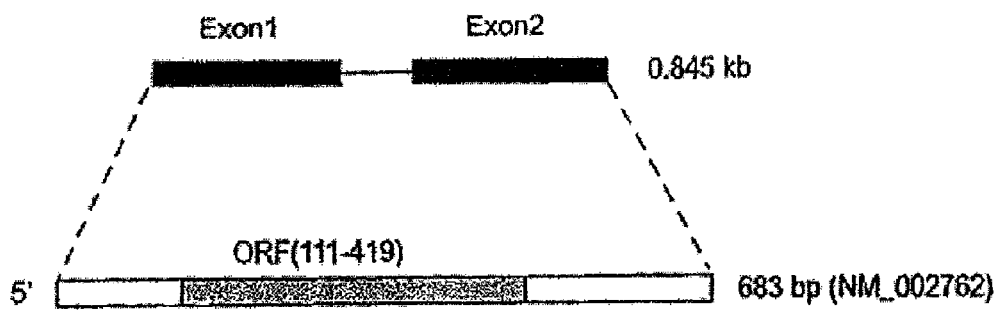
FIG. 5A. Schematic representation of the genomic structure, mRNA, and protein structure of tumor antigen PV13 (protamine 2, GenBank accession number: NM_002762).

Another identified clone had a 737 bp insert. This clone was identical to protamine 2 (Prm2) (GenBank accession: NM_002762) (FIG. 5A). The Protamine 2 gene spans 0.85 kb with 2 exons. The protamine 2 is a spermatid-specific basic protein with 102 aa with a molecular size of 13 kD, which was thus referred to as PV13. PV13 was previously found to be one of the major DNA-binding proteins in sperm, and functional in packaging of DNA in a small volume (A. Balhorn, Protamine mediated condensation of DNA in mammalian sperm: Cache River, Vienna, Ill.; 1999.).

Figure 5B:
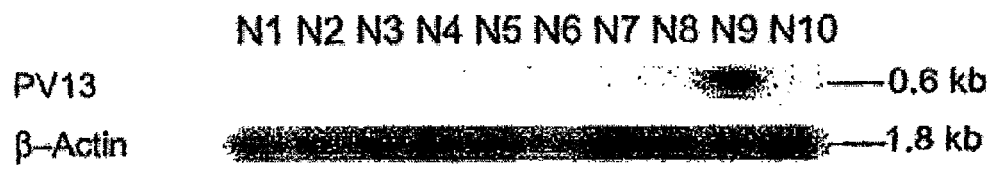
FIG. 5B. The expression of PV13 transcripts in normal tissues detected by Northern blot. The lanes N1 to N10 indicate various normal tissues in the order of brain (N1), liver (N2), placenta (N3), small intestine (N4), colon (N5), thymus (N6), spleen (N7), prostate (N8), testis (N9), and ovary (N10), respectively. The hybridization analyses of the normal tissue and tumor cell expression (BD Clontech) with 32P-labelled specific probes, as indicated, were performed, respectively. The transcript sizes are indicated with kilobases (kb).
Figure 5C:
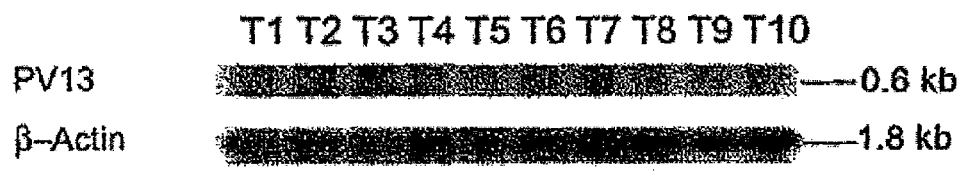
FIG. 5C. The expression of PV13 transcripts in tumor cells detected by Northern blot. The lanes T1 to T10 indicate various tumor cells in the order of acute T cell leukemia (Jurkat cells) (T1), Burkitt's lymphoma (CA46) (T2), breast cancer (MDA-MD-453) (T3), Burkitt's lymphoma (Namalwa) (T4), epidermal carcinoma (A-431) (T5), uterine carcinoma (MES-SA) (T6), Burkitt's lymphoma (Raji) (TI), osteosarcoma (MG-63) (T8), histiocytic lymphoma (U-937) (T9), and cervical adenocarcinoma (Hela S3) (T10), respectively.

In addition, the Northern blot analyses showed that expression of protamine 2 in 10 normal tissues was restricted to testis (N1-N10, FIG. 5B). In contrast, high expression was found in tumor cells (FIG. 5C), especially in acute T cell leukemia (T1), Burkitt's lymphoma (T2, T4, and T7), breast carcinoma (T3), and uterine carcinoma (T6). These results suggested that protamine 2 upregulation in tumor cells was not as pronounced as that of self-tumor antigens CML66 (X. F. Yang et al., CML66, a broadly immunogenic tumor antigen, elicits a humoral immune response associated with remission of chronic myelogenous leukemia, Proc Natl Acad Sci USA 98(2001) 7492-7497.) and CML28 (F. Yang et al., CML28 is a broadly immunogenic antigen, which is overexpressed in tumor cells, Cancer Res 62(2002) 5517-5522.). As reported previously (K. Steger et al., Protamine-1 and -2 mRA in round spermatids is associated with RNA-binding proteins, Histochem Cell Biol 117(2002) 227-234.), the technical problem in differentiating PV13 genomic DNA and PV13 cDNA prevented us from performing quantitative PCR on RNA samples from patients with PV, however, aberrant upregulation of testis antigen protamine 2 in the PV malignant clones might result in the increased immunogenicity of this antigen in patients with PV enhanced by IFN-α therapy.

Figure 5D:
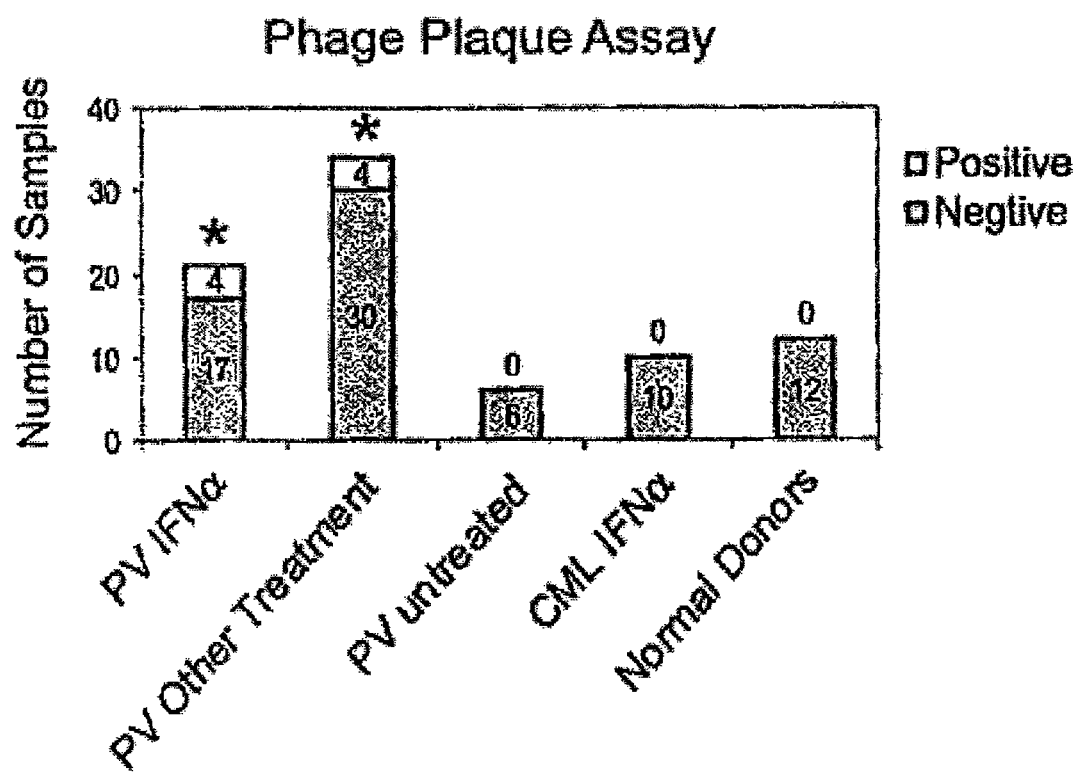
FIG. 5D. The IgG antibody reactions to the tumor antigen PV13 detected by phage plaque assay. The detection rates in each group are presented with the empty column as the positive (on the top) and the solid column as the negative (on the bottom). The experiments were repeated for three times. The representative results are shown. The groups, whose detection rates of the IgG antibody reactions to PV13 are statistically higher than that of healthy donors (the Chi-Square Goodness-of-Fit Test; p<0.05), are marked with *.

The results from phage plaque assay showed that PV13 was not recognized by sera from normal healthy donors, suggesting that they were authentic tumor-associated antigens (FIG. 5D). In contrast, IgG antibody reactions to PV13 was detected in 19.1% of patients with PV who were treated by IFN-α, and in 11.8% of patients with PV who received other treatments, which was significantly higher than the reaction rates in healthy donors (p<0.05) (FIG. 5D). Of note, anti-PV13 IgG antibodies were not detected in the samples from six patients with PV who have not received any treatment (FIG. 5D). Because of the limited number in this group, it was difficult to make a statistical comparison between the untreated group of PV patients and the two groups of PV patients receiving IFN-α and other therapies in detection of anti-PV13 IgG antibodies. Furthermore, similar to antigen PV65. in comparison to patients with PV, IgG antibody reactions to PV13 were not detected in ten patients with CML who received IFN-α treatment (p<0.05), suggesting that humoral reactions to PV13 might play a specific role in patients with PV.

Finally, similar to PV65, there were no significant differences in the detection of IgG antibody reactions to PV13 among the PV patients receiving the therapeutics other than IFN-α (not shown). These results suggested that the immunogenicity of PV13 was significantly enhanced in patients with PV who received IFN-α and other therapies.

Interferon-α

Interferon-α (IFN-α), a pleiotropic cytokine, is widely used in cancer therapy (Lengfelder E., U. Berger and R. Hehlmann. 2000. Interferon alpha in the treatment of polycythemia vera. Ann. Hematol. 79:103). IFN-α therapy induces a clinical remission with documented reversal of clonal hematopoiesis to polyclonal hematopoiesis in polycythemia vera (PV) patients, thus making PV a model to study the antigenic mechanism of the cytokine-enhanced immune responses. Similarly, ~25% of patients with chronic myeloid leukemia (CML), another myeloproliferative disease (MPD), treated with IFN-α undergo a cytogenetic remission. In addition to its direct cytotoxic effects on tumors, IFN-α has been shown to enhance anti-tumor immune response. Cytogenetic response to IFN-α therapy in CML is often associated with therapy-related autoimmunity, indicating that anti-self antigen immune responses induced by IFN-α will play an important role in controlling these diseases. The mechanism of IFN-α regulation of the expression of self-antigens (Wu C. J., X. F. Yang, S. Mclaughlin, D. Neuberg, C. Canning, B. Stein, E. P. Alyea, R. J. Soiffer, G. Dranoff and J. Ritz. 2000. Detection of a potent humoral response associated with immune-induced remission of chronic myelogenous leukemia. J. Clin. Invest. 106:705.) remains largely unknown.

IFN-α has been shown to enhance anti-tumor immune response. However, the self-antigen targets and the mechanism of IFN-α inducing anti-tumor immune response remain poorly defined. The reversion of clonal to polyclonal hematopoiesis in PV patients who responded to IFN-α therapy has been reported. These studies have laid a foundation for definition of therapeutic immune responses in patients with PV. Further, current studies indicate that multiple genetic defects may be involved in the pathogenesis of PV, reflecting tumor heterogeneity and presumably antigen heterogeneity. Therefore, it would beneficial for the antigen-specific based vaccine and other therapeutic approaches to encompass a broader array of tumor antigens to affect broad subpopulations of tumor cells that may express different tumor antigens. The gain-of-function acquired somatic mutation (V617F) of the tyrosine kinase JAK2 has been identified in most patients with PV and other MPDs. It remains to be determined if the activating mutation of JAK2 may modulate the expression of tumor antigens and anti-tumor immune responses, a subject currently under investigation.

To determine the novel mechanisms underlying self-antigen immunogenicity, the inventor focused on RNA transcription and processing. The canonical scanning mechanism has been utilized for the translation initiation of more than 90% mRNAs in eukaryotic cells in recruiting ribosomes at the capped 5'end of mRNAs. Internal ribosome entry sites (IRES) are highly structured regions located within the untranslated region that enable ribosomes to initiate translation effectively (X. F. Yang et al., A novel Bcl-x isoform connected to the T cell receptor regulates apoptosis in T cells, Immunity 7(1997) 629-639.). It is estimated that up to 10% of all mRNAs have the capability to initiate translation by this mechanism (B. Ng et al., Increased non-canonical splicing of autoantigen transcripts provides the structural basis for expression of untolerized epitopes., J Allergy and Clin Immunol December 2004 (2004).). These mRNAs can utilize IRES to promote the translation of downstream cryptic cistron. It has become clear that IRESs are very important component of protein expression in various essential organismal and cellular processes including development, cell cycle and apoptosis.

SEREX

Development of SEREX has led to rapid identification of a large number of tumor antigens deposited in the SEREX database. In contrast, a modest number of tumor antigens have been targeted in tumor vaccines and immunotherapies (Romeo G. et al. 2002. IRF-1 as a negative regulator of cell proliferation. J. Interferon Cytokine Res. 22:39.). Several steps of analysis are mandatory to evaluate SEREX-defined antigens before they become new target antigens for active immunotherapy, including expression analysis, and serological analysis with sera from tumor patients and normal individuals, etc. As a result, a few tumor antigens have yet be exploited in immunotherapy. Demand for new antigen-specific immunotherapies and current technical problems all call for urgent development of new, high through-put technology in mapping immunodominant T cell antigen epitopes, characterization of more clinically targetable antigens from the database, and elucidation of novel mechanisms underlying the immunogenicity of tumor antigens, as is disclosed in the instant invention.

By applying the SEREX technique to screen a human testis expression cDNA library with sera from PV patients, the Inventor identified novel SEREX antigens that elicits potent humoral immune responses in a subset of patients with MPD. The cryptic antigen peptides encoded by introns or UTRs can elicit T cell responses, but also demonstrated that unconventional cryptic antigen peptides can elicit IgG antibody responses. The invention provides novel antigens MPD5, PV13 and PV65 and show that the expression is IRES-mediated. Since these unconventional antigens are small peptides, they require only minimal processing to yield the peptide sizes suitable for MHC class I, class II restricted, and anti-body-recognized antigen epitopes in order to effectively expand self-antigen repertoire. In addition, although short peptide antigens may have the disadvantage of being presented in fewer MHC allelic molecules, they may possess an advantage of being not very immunogenic, which may lead to antigen-specific anergy in patients with tumors. The upregulation of IRES-initiated translation by IFN-α provides new insight into the mechanism of regulating the self-antigen repertoire in response to IFN-α. The demonstration of tumor associated antibody responses elicited by a novel IRES-mediated translation of unconventional antigen is the first such study in tumor immunology.

IFN-α treatment induces upregulation of numerous genes in tumor cells and other cells. However, proteins upregulated by IFN-α may not necessarily all become self-tumor antigens. The overexpression of self-antigens must overcome the "threshold" of antigen concentration at which an immune response is initiated as Zinkernagel et al. recently suggested. In addition, overexpressed antigens must access the antigen presentation pathway and immune system by the following mechanisms. First, overexpressed antigens may be released from damaged tumor cells due to spontaneous necrosis or apoptosis, and then become available in the extracellular environment for attack by the immune cells, potentially through cross-presentation; second, tumor expressed antigens can translocate across the intracellular membranes via binding to heat shock protein 70 and enter the membrane exosome for MHC class II antigen presentation pathway. Moreover, some other factors contributing to the immunogenicity of autoantigens and self-tumor antigens have also been proposed.

Translation

There are two mechanisms used by eukaryotic cells to initiate translation, the classical 7methyl guanosine cap-dependent scanning mechanism and internal ribosome entry site (IRES). IRESs are diverse cis-acting RNA sequences which are able to mediate internal entry of the 40S ribosomal subunit directly onto an AUG or other start codons of eukaryotic and viral messenger RNAs. IRESs are often found in essential mRNAs encoding regulatory proteins (transcription factors, growth factors, and kinases). IRES activity can be modulated in response to mitotic stimuli, hypoxia and other stimuli, p38 MAPK signaling, GM-CSF, and IL-3 via the PI3 kinase pathway (84), which indicate that IRES-containing transcripts are important determinants of cellular proliferation and/or differentiation.

Identification of novel cryptic self-antigen peptides improves our understanding of the self-antigen repertoire. The activation of PKR by IFN-α could induce hepatitis C virus internal ribosome entry site (IRES)-dependent mRNA translation from dicistronic constructs, analogous to our observation that the IRES mediated EGFP translation was increased in responses to IFN-α stimulation. IFN-α-induced, double-stranded (ds) RNA-activated PKR is a key mediator of the antiviral and anti-proliferative effects of IFN-α, thus IFN-α activates IRES-dependent translation of MPD5, PV13, and PV65.

Nucleic Acids

One aspect of the present invention is the polynucleotide sequences essentially as set forth in SEQ ID NO: 1, SEQ ID NO: 3, SEQ ID NO: 5, SEQ ID NO: 18, SEQ ID NO: 19, the complement of these sequences, the RNA versions of both DNA strands and the information otherwise contained within the linear sequence of these polynucleotide sequences, and fragments thereof. The polynucleotide encoding MPD5 is exemplified by SEQ ID NO: 1, SEQ ID NO: 18, and/or SEQ ID NO: 19. The polynucleotide encoding PV65 is exemplified by SEQ ID NO: 3. The polynucleotide encoding PV13 is exemplified by SEQ ID NO: 5. In the case of nucleic acid segments, sequences for use with the present invention are those that have greater than about 50 to 60% homology with any portion of the polynucleotide sequences described herein, sequences that have between about 61% and about 70%; sequences that have between about 71 and about 80%; or between about 81% and about 90%; or between about 91% and about 99%; or which contain nucleotides that are identical, functionality equivalent, or functionally irrelevant, with respect to the nucleotides present in SEQ ID NO: 1, SEQ ID NO: 3, SEQ ID NO: 5, SEQ ID NO: 18, SEQ ID NO: 19, are considered to be essentially similar. Also encompassed within the present invention are nucleic acids that encode polypeptides that are at least 40% identical or similar to the amino acid sequences shown in SEQ ID NO: 2, SEQ ID NO:4, SEQ ID NO:6, and SEQ ID NO: 17.

The invention also encompasses other nucleic acids or nucleic acid like molecules that are sufficient in any regard to mimic, substitute for, or interfere with the polynucleotide sequences, as exemplified by SEQ ID NO: 1, SEQ ID NO: 3, SEQ ID NO: 5, SEQ ID NO: 18, SEQ ID NO: 19, or fragments thereof. It will also be understood that the nucleic acid and amino acid sequences may include additional residues, such as additional 5'- or 3'-sequences, and yet still be essentially as set forth in one of the sequences disclosed herein, so long as the sequence meets the criteria set forth, including the maintenance of functionality.

Included within the invention are DNA or RNA segments including oligonucleotides, polynucleotides and fragments thereof, including DNA or RNA or nucleic acid-like sequences of genomic or synthetic origin, single or double stranded. The invention includes nucleic acid molecules, or nucleic acid-like molecules that are able to hybridize to the sequences in SEQ ID NO: 1, under stringent or under permissive hybridization conditions, or to the complement of said sequences.

The invention also includes oligonucleotide, or oligonucleotide-like sequences such as phosphorthioate, or peptide nucleic acid sequences, which possess sufficient similarity with the sequences disclosed herein such that they are able to stably hybridize to the disclosed sequences, or their complements. Such sequences may be intended as antisense regulators of gene expression, or for the selective amplification or extension of adjoining sequences, for instance by PCR using a given annealing temperature, as would be determined by someone skilled in the art. In addition to the sequences disclosed here, related sequences in other organisms, or homologs, will be readily identified by hybridization using the present sequences. Similar techniques will also apply to the identification of mutant alleles, polymorphisms, deletions, insertions, and so forth, in genomic and cDNA sequences. Whole or partial sequences referred to above may also be identified and isolated using techniques that involve annealing of short oligonucleotides to complementary sequences, such as those as might be present in the genomic DNA of a particular organism, or in genomic or cDNA, including expression cDNA, libraries. Thus, PCR is used to obtain DNA sequences homologous to, and which lie between, two primers, usually between 15 to 30 nucleotides which have annealing temperatures typically between 60-80 degrees Celsius may be substantially purified.

It will be understood that this invention is not limited to the particular nucleic acid sequences presented herein. Recombinant vectors, including for example plasmids, phage, viruses, and other sequences, and isolated DNA or RNA segments may therefore variously include the MPD5, PV13, and PV65 gene sequences or their complements, and coding regions, as well as those that may bear selected alterations or modifications that nevertheless include MPD5, PV13, and PV65 segments or may encode biologically or experimentally relevant amino acid sequences. Such sequences may be created by the application of recombinant DNA technology, where changes are engineered based on the consideration of the nucleotides or amino acids being exchanged, deleted, inserted, fused, or otherwise modified.

Proteins and Polypeptides

One aspect of the invention is the protein, polypeptide, oligopeptide, or amino acid sequences or fragments thereof, of MPD5, essentially as set forth in SEQ ID NO: 2. The MPD5 polypeptide is exemplified by SEQ ID NO: 2. One aspect of the invention is the protein, polypeptide, oligopeptide, or amino acid sequences or fragments thereof, of PV65, essentially as set forth in SEQ ID NO: 4. The PV65 polypeptide is exemplified by SEQ ID NO: 4. One aspect of the invention is the protein, polypeptide, oligopeptide, or amino acid sequences or fragments thereof, of PV13, essentially as set forth in SEQ ID NO: 6. The PV13 polypeptide is exemplified by SEQ ID NO: 6. One aspect of the invention is the protein, polypeptide, oligopeptide, or amino acid sequences or fragments thereof, of MPD5 peptide, essentially as set forth in SEQ ID NO: 17. The MPD5 peptide is exemplified by SEQ ID NO: 17. Sequences that have greater than about 40-50% homology with any portion of the amino acid sequences described herein, sequences that have between about 51% and about 60%; sequences that have between about 61% and about 70% sequences that have between about 70 and about 80%; or between about 81% and about 90%; or between 91% and about 99%; or those that contain amino acids that are identical, functionally equivalent, or functionally irrelevant, for instance those specified by conservative, evolutionarily conserved, and degenerate substitutions, with respect to the amino acid sequences presented in SEQ ID NO: 2 are included. The invention thus applies to MPD5, PV65, and/or PV13 polypeptide sequences, or fragments thereof, and nucleic acids which encode such polypeptides, such as those of other species. Reference is particularly, but not exclusively, made to the conserved regions of MPD5, PV65, and/or PV13, in contrast to similarity throughout the entire length. The invention thus encompasses amino acid sequences, or amino acid-like molecules, that are sufficient in any regard to mimic, substitute for, or interfere with the MPD5, PV65, and/or PV13 amino acid sequences, or fragments thereof.

The invention encompasses MPD5, PV65, and/or PV13 amino acid sequences that have been altered in any form, either through the use of recombinant engineering, or through post-translational or chemical modifications, including those that may be produced by natural, biological, artificial, or chemical methods. Naturally, it will be understood that this invention is not limited to the particular amino acid sequences presented herein. Altered amino acid sequences include those which have been created by the application of recombinant technology such that specific residues, regions, or domains have been altered, and which may be functionally identical, or which may possess unique biological or experimental properties with regards to function or interactions with natural and artificial ligands.

For instance such modifications may confer longer or shorter half-life, reduced or increased sensitivity to ligands that modify function, ability to detect or purify polypeptides, solubility, and so forth. Alternatively, such sequences may be shorter oligopeptides that possess an antigenic determinant, or property that interferes, or competes, with the function of a larger polypeptide, and those that affect interactions between MPD5, PV65, and/or PV13 and other proteins, other nucleic acid regions, and other proteins. Such sequences may be created by the application of the nucleotides or amino acids being exchanged, deleted, inserted, fused, or otherwise modified. Likewise, the current invention within, the sequences that may be naturally present as extensions of, or insertions within, the sequences disclosed herein, including alternative or longer N- and C-terminal sequences, or alternatively spliced protein isoforms.

Production and purification of polypeptides may be achieved in any of a variety of expression systems known to those skilled in the art, including recombinant DNA techniques, genetic recombination, and chemical synthesis. For instance, expression in prokaryotic cells may be achieved by placing protein coding nucleic sequences downstream of a promoter, such as T7, T3, lacI, lacZ, trp, or other cellular, viral, or artificially modified promoters including those that may be inducible by IPTG, tetracycline, maltose, and so forth. Such promoters are often provided for in commercially available recombinant DNA vectors such as pRSET ABC, pBluescript, pKK223-3, and others, or are easily constructed to achieve such a purpose, and often include the presence of multiple cloning sites (MCS) to facilitate typically contain efficient ribosome binding sites, and in some cases transcription termination signals.

Peptides, oligopeptides and polypeptides may also be produced by chemical synthesis, for instance solid phase techniques, either manually or under automated control such as Applied Biosystems 431 peptide synthesizer (Perkin Elmer). After synthesis, such molecules are often further purified by preparative high performance liquid chromatography. Thus, the invention provides methods for the production of epitopes for antibody production, or the production of small molecules that enhance or interfere with a specific function or interaction of the MPD5, PV65, and/or PV13 polypeptides.

Methods to produce and purify said polypeptides in eukaryotic systems are widely available and understood by those proficient in the art. Cells for such production are known to include yeast and other fungi, *Drosophila* and Sf9 cells, cells of other higher eukaryotic organisms such as HeLa, COS, CHO and others, as well as plant cells. Similarly, expression could be achieved in prokaryotic or eukaryotic extracts that are able to translate RNAs into proteins, such as rabbit reticulocyte lysates.

Vectors

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®. 2.0 from INVITROGEN® and BACPACK® BACULOVIRUS EXPRESSION SYSTEM FROM CLONTECH.

Vectors may be of bacterial origin, which may comprise a promoter of a bacteriophage such as phage or T7 which is capable of functioning in the bacteria. In one of the most widely used expression systems, the nucleic acid encoding the MPD5, PV65, and/or PV13 peptides may be transcribed from the vector by T7 RNA polymerase (Studier et al, Methods in Enzymol. 185: 60-89, 1990). In the *E. coli* BL21 (DE3) host strain, used in conjunction with pET vectors, the T7 RNA polymerase is produced from the 1-lysogen DE3 in the host bacterium, and its expression is under the control of the IPTG inducible lac UV5 promoter. This system has been employed successfully for over-production of many proteins. Alternatively, the polymerase gene may be introduced on a lambda phage by infection with an int-phage such as the CE6 phage, which is commercially available (Novagen, Madison, USA).

Other vectors include vectors containing the lambda PL promoter such as PLEX® (Invitrogen, NL), vectors containing the trc promoters such as pTrcHisXpress® (Invitrogen), or pTrc99 (Pharmacia Biotech, SE), or vectors containing the tac promoter such as pKK223-3 (Pharmacia Biotech), or PMAL (New England Biolabs, MA, USA).

One of skill in the art will understand that cloning also requires the step of transforming a host cell with a recombinant nucleic acid molecule. A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer. For example, bacterial host cells, such as *E. coli* HB101, can be transformed by electroporation using any commercially-available electroporation apparatus known in the art, such as a GenePulser apparatus (Bio-Rad, Hercules, Calif.). In one embodiment, mammalian cells, such as BHK-21 cells or Vero cells (ATCC CCL-81), are transformed with a recombinant plasmid containing a cloned cDNA by the method of "transfection." The term "transfection" refers to the transfer of genetic material into a eukaryotic cell, such as a mammalian cell, from the external environment of the cell.

One of skill in the art will appreciate the variety of methods of transfection that are available in the art. Such methods include the nucleic acid/CaPO4 co-precipitation method, the diethylaminoethyl (DEAE)-dextran method, the polybrene method, the cationic liposome method ("lipofection"), the electroporation method, the microinjection method, and the microparticle bombardment method. A description of transfection methods can be found in M. A. Aitken et al., Molecular Biomethods Handbook, Chapter 20, p. 235-250.

According to another embodiment of the instant invention, in vitro transcription is carried out on a recombinant plasmid carrying a cloned cDNA of the invention, under the control of an expressible promoter (i.e., a promoter which is effectively enabled or activated in vitro in the presence of corresponding transcription factors and RNA polymerase). The transcription process generates a fully-infectious mRNA transcript that can be used to transfect (i.e., infect) a cell host, such as BHK-21 (hamster kidney cells) or Vero cells. In one embodiment, the cDNA is operably linked with the bacteriophage transcriptional promoter, T7; to enable the in vitro transcription of the cDNA using bacteriophage T7 DNA-dependent RNA polymerase. One of ordinary skill in the art will appreciate that any suitable promoter, such as, for example, SP6, T3, any bacterial, viral, phage, or eukaryotic promoter, for controlling the transcription of, for example, the MPD5, PV65, and/or PV13 genes, or fragment thereof, and for controlling the expression of a nucleotide sequence encoding a reporter is contemplated by the present invention. It will be appreciated that the promoter is typically selected from promoters which are functional in mammalian cells susceptible to infection by the MPD5, PV65, and PV13 genes, or fragment thereof, encoding sequences of the invention, although prokaryotic or phage promoters and promoters functional in other eukaryotic cells may be used. The promoter is typically derived from promoter sequences of viral or eukaryotic genes. For example, it may be a promoter derived from the genome of a cell in which expression or transcription of, for example, the MPD5, PV65, and/or PV13 gene, or fragment thereof, encoding sequence or construct is to occur.

With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). Tissue-specific or cell-specific promoters specific for lymphocytes, dendritic cells, skin, brain cells and epithelial cells, for example the CD2, CD11c, keratin 14, Wnt-1 and Rhodopsin promoters, respectively. Preferably the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter, the human cytomegalovirus (CMV) IE promoter, or SV40 promoter.

It may also be advantageous for the promoters to be inducible so that the levels of expression of, for example, the MPD5, PV65, and/or PV13 gene, or fragment thereof encoding sequence can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above. It will be appreciated that the sources of promoter sequences, which typically can be retrieved using recombinant techniques from different cloning vectors and plasmids, etc., can be obtained from commercial sources, such as, NEW ENGLAND BIOLABS, INC. (MA), PROMEGA CORPORATION (WI), or BD BIOSCIENCES (CA), or from the laboratories of academic research groups upon request.

The invention also relates to cells which contain such recombinant constructs, where the host cell refers to mammalian, plant, yeast, insect, or other eukaryotic cells, or to prokaryotic, or archae, and vectors that are designed for a given host. Promoter-vector combinations could be chosen by a person skilled in these arts. In some cases, the desired outcome may not be protein, but RNA, and recombinant vectors would include those with inserts present in either forward or reverse orientations.

Many of the vectors and hosts have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP), and so forth which facilitate purification. Vectors may also be designed which contain elements for polyadenylation, splicing and termination, such that incorporation of naturally occurring genomic DNA sequences that contain introns and exons can be produced and processed, or such that unrelated introns and other regulatory signals require RNA processing prior to production of mature, translatable RNAs. Proteins produced in the systems described above could be subject to a variety of post-translational modifications, such as glycosylation, phosphorylation, nonspecific or specific proteolysis or processing.

Purification of MPD5, PV65, and/or PV13, or variants produced as described above can be achieved by any of several widely available methods. Cells may be subject to freeze-thaw cycles or sonication to achieve disruption, or may be fractionated into subcellular components prior to further purification. Purification may be achieved by one or more techniques such as precipitation with salts or organic solvents, ion exchange, hydrophobic interaction, HPLC and FPLC chromatograpic techniques. Affinity chromatographic techniques could include the use of polyclonal or monoclonal antibodies raised against the expressed polypeptide, or antibodies raised against or available for an epitopic tag such as HA or FLAG. Similarly, purification can be aided by affinity chromatography using fusions to the desired proteins such as GSH-affinity resin, maltose affinity resin, carbohydrate (lectin) affinity resin or, in a one embodiment, Ni-affinity resin, and so forth. In some instances purification is achieved in the presence of denaturing agents such as urea or guanidine, and subsequent dialysis techniques may be required to restore functionality, if desired.

Any method of in vitro transcription known to one of ordinary skill in the art is contemplated by the instant invention. It will be understood that the method of in vitro transcription of a DNA sequence relies on the operable linkage to an appropriate promoter and that the cognate RNA polymerase is used to direct transcription of the DNA starting at the promoter sequence. It will be further appreciated that the RNA polymerase and promoter can be of bacterial, eukaryotic, or viral (including bacteriophage) origin. Bacteriophage-RNA polymerases are very robust, and the availability of purified recombinant proteins facilitates the generation of large quantities of RNA from cloned cDNA sequences. In contrast, eukaryotic in vitro transcription systems yield relatively small quantities of RNA. Bacteriophage-RNA polymerases, such as from bacteriophages SP6, T7, and T3, are especially suitable for the generation of RNA from DNA sequences cloned downstream of their specific promoters because, first, their promoters are small and easily incorporated into plasmid vectors and second, the polymerases are quite specific for their cognate promoters, which results in very little incorrect transcriptional initiation from DNA templates. Any suitable promoter, however, is contemplated by the instant invention, including, for example, bacterial, phage, viral, and eukaryotic promoters. Strong termination sequences are not available for these polymerases so that DNA templates can be linearized with a restriction enzyme 3' to the desired end of the RNA transcript and the polymerase is forced to stop at this point-a process referred to as "run-off" transcription. A full description of in vitro transcription can be found in M. A. Aitken et al., Molecular Biomethods Handbook, Chapter 26, p. 327-334 and Sambrook, J. and D. W. Russell, Molecular Cloning: A Laboratory Manual, Third Edition (2001).

The invention provides a dual luciferase reporter system for measuring recoding efficiencies in vivo or in vitro from a single construct see U.S. Pat. No. 6,143,502 (Grentzmann et al.). For example, the firefly luciferase gene (fluc) has been cloned behind the renilla luciferase gene (rluc) into an altered vector pRL-SV40 vector (Promega Corp., Madison, Wis.; catalog no. TB239). Other reporter genes may also be used, for example, green fluorescent protein, and variants thereof. Expression features for initiation and termination of transcription and translation, as well as the nature of the two reporter genes (short enough to be efficiently synthesized in an in vitro translation system), allow application of the same reporter construct for in vivo and in vitro applications. Between the 5'reporter (rluc) and the 3'reporter (fluc) two alternative polylinkers have been inserted, yielding p2luc and p2luci. The p2luc polylinker has restriction sites for digestion with SalI, BamHI, and SacI, whereas the p2luci polylinker has restriction sites for digestion with SalI, ApaI, BglII, Eco47III, BamHI, SmaI, and SacI. The assay using these reporter plasmids combines rapidity of the reactions with very low background levels and provides a powerful assay. In vitro experiments can be performed in 96-well microtiter plates, and in vivo experiments can be performed in 6-well culture dishes. This makes the dual-luciferase assay suitable for high throughput screening approaches.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK® Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12, etc. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Diagnostic Systems and Kits

A diagnostic system in kit form of the present invention includes, in an amount sufficient for at least one assay, a polypeptide, antibody composition or monoclonal antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention. The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems. The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium or $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

The diagnostic kits of the present invention can be used in an "ELISA" format to detect, for example, the presence or quantity of MPD5, PV65, and/or PV13 in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

Thus, in preferred embodiments, a polypeptide, antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used. Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. In one embodiment a diagnostic system of the present invention is useful for assaying for the presence of MPD5, PV65, and/or PV13. Such a system comprises, in kit form, a package containing an antibody to MPD5, PV65, and/or PV13.

Vaccine

Another aspect of the invention relates to a method for inducing an immunological response in an individual, particularly a mammal which comprises inoculating the individual with, for example, MPD5, PV65, and/or PV13, or a fragment or variant thereof. Also provided are methods whereby such immunological response slows bacterial replication. Yet another aspect of the invention relates to a method of inducing immunological response in an individual which comprises delivering to such individual a nucleic acid vector to direct expression of, for example, an MPD5, PV65, and/or PV13, or a fragment or a variant thereof, for expressing, for example, MPD5, PV65, and/or PV13, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to, for example, an MPD5, PV65, and/or PV13 gene, or protein coded therefrom, wherein the composition comprises, for example, a recombinant MPD5, PV65, and/or PV13 gene, or protein coded therefrom comprising DNA which codes for and expresses an antigen of said MPD5, PV65, and/or PV13 or protein coded therefrom. The immunological response may be used therapeutically or prophylactically and may take the form of antibody immunity or cellular immunity such as that arising from CTL or CD4+T cells.

In an exemplary embodiment, an MPD5, PV65, and/or PV13 polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

The invention also includes a vaccine formulation which comprises an immunogenic recombinant protein of the invention together with a suitable carrier. the invention also provides that these formulations may be provided in kit form. The vaccine may for example, be administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain MPD5, PV65, and/or PV13 protein, it is to be understood that this covers fragments of the naturally occurring protein and similar proteins with additions, deletions or substitutions which do not substantially affect the immunogenic properties of the recombinant protein.

Target Antigens

An embodiment of the present invention relates to an antibody that binds to an MPD5 protein. An exemplary amino acid sequence of MPD5 protein is shown in SEQ ID NO: 2. An exemplary amino acid sequence of MPD5 peptide is shown in SEQ ID NO: 17. That is, an antibody according to the first embodiment of the present invention is preferably an antibody that specifically binds to, for example, the MPD5 protein or peptide. Full length MPD5 protein is exemplified in SEQ ID NO: 2, and variants, fragments, muteins, etc., and those proteins derived from this protein. MPD5 peptide is exemplified in SEQ ID NO: 17, and variants, fragments, muteins, etc., and those proteins derived from this peptide. It is known that humans have a diversity of allele mutations and those proteins with one or more amino acids substituted, deleted, inserted, or added are also included in the MPD5 protein. However, it is not limited to these. It is known that humans have a diversity of allele mutations and those proteins with one or more amino acids substituted, deleted, inserted, or added are also included in the MPD5 protein. However, it is not limited to these.

An embodiment of the present invention relates to an antibody that binds to an PV65 protein. A typical amino acid sequence of PV65 protein is shown in SEQ ID NO: 4. That is, an antibody according to the first embodiment of the present invention is preferably an antibody that specifically binds to, for example, the PV65 polypeptide. Full length PV65 protein is exemplified in SEQ ID NO: 4, and variants, fragments, muteins, etc., and those proteins derived from this protein. It is known that humans have a diversity of allele mutations and those proteins with one or more amino acids substituted, deleted, inserted, or added are also included in the PV65 protein. However, it is not limited to these. It is known that humans have a diversity of allele mutations and those proteins with one or more amino acids substituted, deleted, inserted, or added are also included in the PV65 protein. However, it is not limited to these.

An embodiment of the present invention relates to an antibody that binds to an PV13 protein. A typical amino acid sequence of PV13 protein is shown in SEQ ID NO: 6. That is, an antibody according to the first embodiment of the present invention is preferably an antibody that specifically binds to, for example, the PV13 polypeptide. Full length PV13 protein is exemplified in SEQ ID NO: 6, and variants, fragments, muteins, etc., and those proteins derived from this protein. It is known that humans have a diversity of allele mutations and those proteins with one or more amino acids substituted, deleted, inserted, or added are also included in the PV13 protein. However, it is not limited to these. It is known that humans have a diversity of allele mutations and those proteins with one or more amino acids substituted, deleted, inserted, or added are also included in the PV13 protein. However, it is not limited to these.

Fragments of the MPD5, PV65, and/or PV13 protein may serve as the target antigen for the antibody binding. An example of an MPD5 peptide which may serve as the target antigen is SEQ ID NO: 17, or fragments thereof. These antigen fragments may be about 6, 7, 8, 9, 10, 11, 12, 13, 14, 15, 16, 17, 18, 19, or 20 amino acids in length. The antigen fragments may by about 10, 20, 30, 40, 50, or 100 amino acids in length. The antibody of the present invention may be either a polyclonal antibody or a monoclonal antibody. To specifically detect a high molecular weight soluble MPD5, PV65, and/or PV13 protein, it is desirable to use antibodies to certain limited epitopes and hence monoclonal antibodies are preferable. Molecule species are not particularly limited. Immunoglobulins of any class, subclass or isotype may be used.

Antibodies and Antibody Compositions

Additionally, the present invention includes a purified antibody produced in response to immunization with MPD5, PV65, and/or PV13, as well as compositions comprising this purified antibody.

Antibodies refer to single chain, two-chain, and multi-chain proteins and glycoproteins belonging to the classes of polyclonal, monoclonal, chimeric, and hetero immunoglobulins; it also includes synthetic and genetically engineered variants of these immunoglobulins. "Antibody fragment" includes Fab, Fab', F(ab')2, and Fv fragments, as well as any portion of an antibody having specificity toward a desired target epitope or epitopes. A humanized antibody is an antibody derived from a non-human antibody, typically murine, that retains or substantially retains the antigen-binding properties of the parent antibody but which is less immunogenic in humans, U.S. Pat. No. 5,530,101, incorporated herein by reference in its entirety.

An antibody composition of the present invention is typically produced by immunizing a laboratory mammal with an inoculum of the present invention and to thereby induce in the mammal antibody molecules having the appropriate polypeptide immunospecificity. The polyclonal antibody molecules are then collected from the mammal and isolated to the extent desired by well known techniques such as, for example, by immunoaffinity chromatography. The antibody composition so produced can be used in, inter alia, the diagnostic methods and systems of the present invention to detect MPD5, PV65, and/or PV13 in a body sample.

Monoclonal antibody compositions are also contemplated by the present invention. A monoclonal antibody composition contains, within detectable limits, only one species of antibody combining site capable of effectively binding MPD5, PV65, and/or PV13. Thus, a monoclonal antibody composition of the present invention typically displays a single binding affinity for MPD5, PV65, and/or PV13 even though it may contain antibodies capable of binding proteins other than MPD5, PV65, and/or PV13. Suitable antibodies in monoclonal form, typically whole antibodies, can also be prepared using hybridoma technology described by Niman et al., Proc. Natl. Sci., U.S.A., 80:4949-4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

The antibody compositions produced by the above method can be used, for example, in diagnostic and therapeutic modalities wherein formation of an MPD5, PV65, and/or PV13-containing immunoreaction product is desired.

Diagnostic Use

In another embodiment of the present invention, measurement of MPD5, PV65, and/or PV13, or proteins which are immunologically related to MPD5, PV65, and/or PV13, can be used to detect and/or stage a disease or disorder in a subject. The measured amount of the soluble molecule or of the total marker is compared to a baseline level. This baseline level can be the amount which is established to be normally present in the body fluid of subjects with various degrees of the disease or disorder. An amount present in the body fluid of the subject which is similar to a standard amount, established to be normally present in the body fluid of the subject during a specific stage of the disease or disorder, is indicative of the stage of the disease in the subject. The baseline level could also be the level present in the subject prior to the onset of disease or the amount present during remission of disease, or from individuals not afflicted with the disease or condition.

The present invention also provides for the detection or diagnosis of disease or the monitoring of treatment by measuring the amounts of MPD5, PV65, and/or PV13 transcript or peptide in a sample before and after treatment, and comparing the two measurements. The change in the levels of the markers relative to one another can be an improved prognostic indicator. A comparison of the amounts of a total marker with the amount of intra-cytoplasmic marker or membrane-bound marker is also envisioned.

The present invention provides a method for monitoring the effect of a therapeutic treatment on a subject who has undergone the therapeutic treatment. This method comprises measuring at suitable time intervals the amount of a soluble molecule or soluble fragment thereof, or the amount of MPD5, PV65, and/or PV13 or fragment thereof. Any change or absence of change in the amount of the soluble molecule or in the amount of the MPD5, PV65, and/or PV13 can be identified and correlated with the effect of the treatment on the subject. In a specific embodiment of the invention, soluble molecules immunologically related to MPD5, PV65, and/or PV13 can be measured in the serum of patients by a sandwich enzyme immunoassay (for an example) in order to predict disease prognosis, for example, in viral infections, inflammation, autoimmune diseases, and tumors, or to monitor the effectiveness of treatments such as anti-viral administration.

The invention will be illustrated in more detail with reference to the following Examples, but it should be understood that the present invention is not deemed to be limited thereto.

The invention will be illustrated in more detail with reference to the following Examples, but it should be understood that the present invention is not deemed to be limited thereto.

EXAMPLES

Serum Samples

In accordance with a protocol approved by the Institutional Review Board at Temple University and established guidelines, serum samples were obtained from patients with PV and CML receiving IFN-α therapy enrolled into Baylor College of Medicine (eight patients with PV receiving IFN-α treatment, 8 PV patients receiving other treatments), A. D. Anderson Cancer Center (! 0 patients with C!\L receiving TFN-(X treatment), New York Presbyterian Hospital-Weill Cornell Medical Center (13 PV patients receiving IFN-α treatment, 26 PV patients receiving other treatments, six PV patients having not yet received any treatments) Institutional Review Board-approved trials. The therapeutic regimens other than IFN-α for the 34 patients with PV included imatinib mesylate (Gleevec, 16 patients), hydroxyurea ci 2 patients), hydroxyurea plus agrelin (three patients), agrelin plus phlebotomy (one patient), phlebotomy (one patient), and thalidomide (one patient). The patients in the other treatment group have not been treated with IFN-α.

Human Testis CDNA Library Screening by SEREX

XL-1 Blue MR' E. coli (Stratagene, La Jolla, Calif.) were infected with the recombinant phages of a human testis expression cDNA library (BD Clontech, Palo Alto, Calif.), and expression of recombinant proteins was induced by incubation with isopropyl β-D-thiogalactoside (IPTG) (Fisher, Pittsburgh, Pa.) treated nitrocellulose membranes (Schleicher & Schuell Bioscience, Keene, N.H.). The filters were then incubated with sera from the PV patients, diluted at 1:500 in TBST at 4 ce. The serum was pre-absorbed against lysate of the phage and the E. coli strain to minimize nonspecific antibody binding (Stratagene). Visualization of the antigen-antibody complex was accomplished by staining with the Sigma Fast™ BCIPINT substrate (Sigma, St Louis, Mo.). DNA sequencing was performed by SeqWright (Houston, Tex.).

In Vitro Transcription and Translation (TNT)

The TNT with plasmid pTriplEx (BD Clontech, Palo Alto, Calif.) containing cDNA encoding sequences and plasmid pTriplEx without cDNA insert (as a negative control) were performed according to the manufacturer's protocol (Promega, Madison, Wis.).

Semi-Quantitative Reverse Transcription (RT)-PCR and PCR Cloning

Human IFN-α ($1\times10^5$ units/100 μl) was purchased from PBL Biomedical Laboratories (Piscataway, N.J.). Stimulation of K562 cells, a human myeloid leukemia cell line, with IFN-α was executed (1000 units/ml) for the indicated time points(11). RT-PCR and PCR cloning were performed, as described (9). A sense primer (PV1ORF5) specific to the 5' sequence of MPD5 (5'-AACAGCAGCCCTTTCTCTCCA GTA-3')(SEQ ID NO: 8) and an antisense primer (PV1ORF3) (5'-TAATACGCAGCAGAGCTGGATT G-3')(SEQ ID NO: 9) specific to the 3' sequence of MPD5 were used for PCR. The PCR products (290 bp) were cloned into pCRII-TOPO vector (Invitrogen). As a control, PCRs were performed for β-actin with a sense primer, HB-actin5 (5'-ATCTGGCAC-CACACCTTCTACAATGAGCTGCG-3')(SEQ ID NO: 10), and an antisense primer, HB-actin3 (5'-CGTCATACTCCT-GCTTGCTGATCCACATCTGC-3')(SEQ ID NO: 11). The signals of PCR products were normalized as relative densitometric units via comparison to β-actin signals amplified in the same cDNA preparations (9). PCR for the amplification of ISG15 was performed with a sense primer, ISG5 (5'-GAGAGGCAGCGAATTCATCT-3')(SEQ ID NO: 12), and an antisense primer, ISG3 (5'-AA GGGGGACCCTGTC-CTG-3')(SEQ ID NO: 13), as a positive control for the genes upregulated by IFN-α stimulation, as reported (11).

Quantitative RT-PCR

Quantitative RT-PCR—used to determine antigenic mRNA in total RNA isolated from peripheral blood granulocytes via TaqMan One-Step RT-PCR Master Mix Reagents (Applied Biosystems, AB, Foster City, Calif.)—was performed on the ABI PRISM 7000 System (AB,)(3). The primers and TaqMan probe for MPD5 were synthesized by AB, including: MPD5-EX1F (forward primer), 5'-GCTGAGAT-TGCGCCACTGTA-3'(SEQ ID NO: 14); MPD5-EX1R (reverse primer), 5'-CCTCTCCT AGGCTCCAAGTGT-3'(SEQ ID NO: 15); and MPD5-EX1M1 (probe labeled with FAM), 5'-TCCAGCCTGGGATTC-3'(SEQ ID NO: 16). Used as the reference standard and labeled with VIC fluorophore (targeted center of sequence: 606 bp), the 18S ribosomal RNA were also purchased from AB. The amount of RNA representing the linear range of response for MPD5 and 18S was employed (i.e., typically, 100 ng-0.01 ng RNA/reaction). PCR without RT was also executed for control. Threshold cycles (CT) at the reporter signal were normalized with the reference gene, 18S (h18S), and ΔCT [$\Delta CT = CT_X - CT_R$, the difference in threshold cycles for the target gene X and the reference (R)] was calculated. Mean ΔCT was compared among groups via ANOVA (Ng, F. Yang, D. P. Huston, Y. Yan, Y. Yang, Z. Xiong, L. E. Peterson, H. Wang, X. F. Yang, Increased noncanonical splicing of autoantigen transcripts provides the structural basis for expression of untolerized epitopes, J Allergy Clin Immunol 114(2004) 1463-1470).

Granulocytes were separated by differential centrifugation and isopyknic density gradient separation using standard protocols. RNA was prepared from granulocytes using TR1 reagent (Molecular Research Center, Cincinnati, Oreg.) in combination with RNeasy mini kit (Qiagen, Valencia, Calif.) according to the manufacturers' protocols to avoid DNA contamination. Quantitative real-time RT-PCR was used to quantify PV65 mRNA in total RNAs isolated from peripheral blood granulocytes using the TaqMan One-Step RT-PCR master mix reagents (Applied Biosystems, Foster City, Calif.) for Real time PCR, which were performed on an ABI Prism 7000 sequence detection system (Applied Biosystems). The primers and TaqMan probe for PV65 with targeted center of sequence at 1402 bp were purchased from Applied Biosystems (Hs00230684). The 18S ribosomal RNA used as a reference was labeled with the VLC fluorophore, targeted to center of the sequence at 606 bp, and also was purchased from Applied Biosystems. Expression of PV65 and 18S was analyzed in separate reactions. An amount of RNA was used which gave a linear range of response for PV65 and 18S (typically 100 fig-0.01 ng RNAIreaction). We used a universal RT-PCR protocol recommended by the manufacturer, that is, reverse transcription at 48° e for 30 minutes, denaturation and polymerase activation at 95° e for 10 minutes, followed by 50 cycles of denaturation at 92° C. for 15 seconds and annealing/extension/plate reading at 60° e for one minute. RT-PCRs for each sample and each gene were done in duplicate. PCR without reverse transcriptase was performed for each sample to control for the possible interference from genomic DNA contamination. The threshold amplification cycles (CT) at the reporter signal was normalized with the reference gene human 18S (hI8S), βCT (βCT=CTx–CTR, the difference in threshold cycles for the target gene X and the reference (R)) was calculated (L. Liu et al., Discrimination of polycythemias and thrombocytoses by novel, simple, accurate clonality assays and comparison with PRV-1 expression and BFU-E response to erythropoietin, Blood 101(2003) 3294-3301.). Mean βCT was compared among each sample group with the ANOV A test (B. Rosner, Multisample Inference Fifth edn. Australia, Canada, Mexico, Sigapore, Spain, United Kingdom, United States: Duxbury; 2000).

Peptide Synthesis and Peptide ELISA

An MPD5-specific peptide was synthesized according to the sequence of MPD5, from aa 30 to aa 47 (N-TLNLST-GQASSPQCLLPS-C)(SEQ ID NO: 17), at Sigma-Genosys (The Woodlands, Tex.). ELISAs were performed (Sacchi, H. Kantarjian, S. O'Brien, P. R. Cohen, S. Pierce, M. Talpaz, Immunemediated and unusual complications during interferon alfa therapy in chronic myelogenous leukemia, J Clin Oncol 13(1995) 2401-2407).

Bioinformatic Analyses

To determine whether cloned sequences were related or identical to genes, proteins, or proteIn domains in the databases, sequence analyses were performed using the NCBI-GenBank databases, NCBI-conserved domain databases, and the PROSITE analysis (Ng, Fan Yang, David P. Huston, Yan Yan, Yu Yang, Zeyu Xiong, LeifE. Peterson, Hong Wang, Xiao-Feng Yang, Increased non-canonical splicing of autoantigen transcripts provides the structural basis for expression of untolerized epitopes., J Allergy and Clin Immunol December 2004(2004)). The gene organizations such as intron, exon, chromosome location, were analyzed through searches in the NCBI-LocusLink website, and the NCBI-AceView website. In addition to the Northern blot analyses, the gene expression data for genes were analyzed by searching the NCBI-UniGene website, and the NCBI-SAGEmap database (SAGE, Serial Analysis of Gene Expression). The cis-acting transcription factor binding sites in promoters of antigens were searched in the TRANSF AC database.

Northern Blot and Southern Blot

Multiple tissue Northern blots were prepared with purified polyadenylated RNAs (2 μg/lane) (Ambion, Austin, Tex.). Hybridizations were conducted with the probes of PV65 and PV13, as reported previously (F.Yang, C. 1. Wu, S. McLaughlin, A. Chilemi, K. S. Wang, C. Canning, E. P. Alyea, P. Kantoff, R. 1. Soiffer, G. Dranoff, 1. Ritz, CML66, a broadly immunogenic tumor antigen, elicits a humoral immune response associated with remission of chronic myelogenous leukemia, Proc Natl Acad Sci USA 98(2001) 7492-7497.).

Phage Plaque Assay

The phage plaque assay was performed as described previously (Wu et al., Detection of a potent humoral response associated with immune-induced remission of chronic myelogenous leukemia, J Clin Invest 106(2000) 705-714.). Phages from positive clones of interest were mixed with the cDNA insert-free phage of the cDNA library (generously provided by Dr. C. J. Wu at Harvard Medical School, MA) as internal negative controls at a ratio of 1:5.

Western Blot

Western blot procedures were performed as described. PV65 (eIF-2α) protein on the blots were visualized, respectively, with 1:1000 diluted eIF-2α antibody (Cell Signaling Technology, Beverly, Mass.), and Phospho-eIF-2α (Ser51) Antibody (Cell Signaling).

Transcriptional Clonality Assay

The genotypes for exonic polymorph isms of 5∴-chromosome genes (MP PI, IDS, G6P D, BTK and FHL1) of three patients with PV were determined. To examine the clonality of hematopoietic cells in these patients before and after IFN-α therapy, the peripheral blood specimens were drawn every three months and RNA was extracted from platelets and granulocytes. The mRNA expression of the informative polymorphic genes were then assayed using single-stranded conformation polymorphism (SSCP) analysis as previously described (L. Liu et al. Discrimination of polycythemias and thrombocytoses by novel, simple, accurate clonality assays and comparison with PRV-1 expression and BFU-E response to erythropoietin, Blood 101(2003) 3294-3301).

While the invention has been described in detail and with reference to specific examples thereof, it will be apparent to one skilled in the art that various changes and modifications can be made therein without departing from the spirit and scope thereof.

What is claimed is:

1. A substantially purified polypeptide consisting of the amino acid sequence of SEQ ID NO:17, wherein the substantially purified polypeptide elicits or enhances an immune response in an individual for a disorder selected from the group consisting of viral infections, inflammation, autoimmune diseases, and tumors, wherein the substantially purified polypeptide is a fusion polypeptide further comprising a sequence selected from the group consisting of polyhistidine tags, HA, FLAG, myc, glutathione S-transferase (GST), and maltose binding protein (MBP), lipoprotein D from *Hemophilus influenzae*, and beta-galactosidase, wherein the substantially purified polypeptide elicits or enhances an immune response in an individual for a disorder selected from the group consisting of viral infections, inflammation, autoimmune diseases, and tumors.

2. A vaccine composition comprising an immunogenic peptide consisting of the amino acid sequence of SEQ ID NO:17, wherein the immunogenic peptide elicits or enhances an immune response in an individual for a disorder selected from the group consisting of viral infections, inflammation, autoimmune diseases, and tumors, wherein the immunogenic peptide is a fusion polypeptide further comprising a sequence selected from the group consisting of polyhistidine tags, HA, FLAG, myc, glutathione S-transferase (GST), and maltose binding protein (MBP), lipoprotein D from *Hemophilus influenzae*, and beta-galactosidase, wherein the immunogenic peptide elicits or enhances an immune response in an individual for a disorder selected from the group consisting of viral infections, inflammation, autoimmune diseases, and tumors.

3. An immunogenic peptide consisting of the amino acid sequence of SEQ ID NO:17, wherein the immunogenic peptide elicits or enhances an immune response in an individual for a disorder selected from the group consisting of viral infections, inflammation, autoimmune diseases, and tumors, wherein the immunogenic peptide is a fusion polypeptide further comprising a sequence selected from the group consisting of polyhistidine tags, HA, FLAG, myc, glutathione S-transferase (GST), and maltose binding protein (MBP), lipoprotein D from *Hemophilus influenzae*, and beta-galactosidase, wherein the immunogenic peptide elicits or enhances an immune response in an individual for a disorder selected from the group consisting of viral infections, inflammation, autoimmune diseases, and tumors.

4. A diagnostic kit for a disorder selected from the group consisting of viral infections, inflammation, autoimmune diseases, and tumors comprising an immunogenic peptide consisting of the amino acid sequence of SEQ ID NO:17, wherein the immunogenic peptide elicits or enhances an immune response in an individual, wherein the immunogenic peptide is a fusion polypeptide further comprising a sequence selected from the group consisting of polyhistidine tags, HA, FLAG, myc, glutathione S-transferase (GST), and maltose binding protein (MBP), lipoprotein D from *Hemophilus influenzae*, and beta-galactosidase, wherein the immunogenic peptide elicits or enhances an immune response in an individual.

5. The substantially purified polypeptide of claim 1, wherein the substantially purified polypeptide is produced by expression in cells selected from the group consisting of yeast cells, *Drosophila* cells, Sf9 cells, plant cells, and prokaryotic cells.

6. The vaccine composition of claim 2, wherein the immunogenic peptide is produced by expression in cells selected from the group consisting of yeast cells, *Drosophila* cells, Sf9 cells, plant cells, and prokaryotic cells.

7. The immunogenic peptide of claim 3, wherein the immunogenic peptide is produced by expression in cells selected from the group consisting of yeast cells, *Drosophila* cells, Sf9 cells, plant cells, and prokaryotic cells.

8. The diagnostic kit of claim 4, wherein the immunogenic peptide is produced by expression in cells selected from the group consisting of yeast cells, *Drosophila* cells, Sf9 cells, plant cells, and prokaryotic cells.

* * * * *

UNITED STATES PATENT AND TRADEMARK OFFICE
CERTIFICATE OF CORRECTION

PATENT NO. : 9,163,088 B2  
APPLICATION NO. : 12/446849  
DATED : October 20, 2015  
INVENTOR(S) : Xiao-Feng Yang Page 1 of 1

It is certified that error appears in the above-identified patent and that said Letters Patent is hereby corrected as shown below:

In the Specification

At Column 1, Lines 18-20, the wording "This research was supported in part by U.S. Government funds (NIH Grant No. AI054514), and the U.S. Government may therefore have certain rights in the invention." should read --This invention was made with government support under AI054514 awarded by the National Institutes of Health. The government has certain rights in the invention.--.

Signed and Sealed this  
Fifteenth Day of August, 2023

Katherine Kelly Vidal  
*Director of the United States Patent and Trademark Office*